United States Patent [19]
Leidner et al.

[11] Patent Number: 6,056,993
[45] Date of Patent: May 2, 2000

[54] POROUS PROTHESES AND METHODS FOR MAKING THE SAME WHEREIN THE PROTHESES ARE FORMED BY SPRAYING WATER SOLUBLE AND WATER INSOLUBLE FIBERS ONTO A ROTATING MANDREL

[75] Inventors: Jacob Leidner, North York; Karim Amellal, Tecumseh, both of Canada

[73] Assignee: Schneider (USA) Inc., Plymouth, Minn.

[21] Appl. No.: 09/062,129

[22] Filed: Apr. 17, 1998

Related U.S. Application Data

[60] Provisional application No. 60/048,091, May 30, 1997.

[51] Int. Cl.$^7$ ............... B05D 1/04; B05D 1/34; B05D 1/06; B05D 3/00
[52] U.S. Cl. ............ 427/2.25; 427/2.3; 427/2.31; 427/184; 427/202; 427/243; 427/353; 427/407.1; 427/425; 427/426; 427/470; 427/462
[58] Field of Search ................. 427/2.25, 2.28, 427/2.3, 2.31, 425, 426, 462, 470, 481, 352, 353, 407.1, 243, 273, 184, 200, 201, 202, 206, 299, 336, 479

[56] References Cited

U.S. PATENT DOCUMENTS

| | | | |
|---|---|---|---|
| 3,491,760 | 1/1970 | Braun et al. | 128/334 |
| 4,193,138 | 3/1980 | Okita | 3/1.4 |
| 4,265,928 | 5/1981 | Braun | 427/2 |
| 4,286,341 | 9/1981 | Greer et al. | 427/2.25 |
| 4,451,568 | 5/1984 | Schneider et al. | 435/181 |
| 4,474,630 | 10/1984 | Planck et al. | 156/62.4 |
| 4,522,753 | 6/1985 | Yannas et al. | 260/123.7 |
| 4,670,286 | 6/1987 | Nyilas et al. | 427/2.25 |
| 4,675,361 | 6/1987 | Ward, Jr. | 525/92 |
| 4,743,258 | 5/1988 | Ikada et al. | 427/2.25 |
| 4,747,848 | 5/1988 | Maini | 623/1 |
| 4,770,664 | 9/1988 | Gogolewski | 427/2.25 |
| 4,774,271 | 9/1988 | Lindner et al. | 523/342 |
| 4,816,339 | 3/1989 | Tu et al. | 428/421 |
| 4,851,009 | 7/1989 | Pinchuk | 427/2.25 |
| 4,871,361 | 10/1989 | Kira | 427/2.25 |
| 4,871,366 | 10/1989 | von Recum et al. | 623/11 |
| 4,892,344 | 1/1990 | Takada et al. | 294/88 |
| 4,902,290 | 2/1990 | Fleckenstein et al. | 427/2.25 |
| 4,976,733 | 12/1990 | Girardot | 623/11 |
| 5,061,276 | 10/1991 | Tu et al. | 623/1 |
| 5,084,065 | 1/1992 | Weldon et al. | 623/1 |
| 5,108,424 | 4/1992 | Hoffman, Jr. et al. | 623/1 |
| 5,116,360 | 5/1992 | Pinchuk et al. | 623/1 |
| 5,163,951 | 11/1992 | Pinchuk et al. | 623/1 |
| 5,298,276 | 3/1994 | Jayaraman | 427/2 |
| 5,376,376 | 12/1994 | Li | 424/443 |
| 5,383,927 | 1/1995 | DeGoicoechea et al. | 623/1 |
| 5,575,818 | 11/1996 | Pinchuk | 623/1 |
| 5,584,875 | 12/1996 | Duhamel et al. | 623/1 |
| 5,584,877 | 12/1996 | Miyake et al. | 623/1 |
| 5,605,696 | 2/1997 | Eury et al. | 424/423 |
| 5,607,478 | 3/1997 | Lentz et al. | 623/12 |
| 5,609,624 | 3/1997 | Kalis | 623/1 |
| 5,609,629 | 3/1997 | Fearnot et al. | 623/1 |
| 5,716,660 | 2/1998 | Weadock et al. | 427/2.25 |
| 5,837,313 | 11/1998 | Ding et al. | 427/2.25 |

FOREIGN PATENT DOCUMENTS

WO 86/02843  5/1986  WIPO.

OTHER PUBLICATIONS

A novel process for the manufacturing of porous grafts: Process description and product evaluation; By Jacob Leidner, Edward W.C. Wong, David C. MacGregor, and Gregory J. Wilson; Journal of Biomedic Materials Research, vol. 17, No. 2, Mar. 1983, pp. 229–247.

*Primary Examiner*—Diana Dudash
*Attorney, Agent, or Firm*—Faegre & Benson, LLP.

[57] ABSTRACT

A porous, tubular synthetic prosthesis, prosthesis precursor, and methods of producing the same are provided. Specifically the method involves co-spraying both a water soluble and water insoluble fibrous component onto a mold to form the prosthesis precursor. The water soluble fibrous component may then be at least partially removed so as to provide a porous, tubular synthetic prosthesis.

22 Claims, 15 Drawing Sheets

POROUS PROTHESES AND METHODS FOR MAKING THE SAME WHEREIN THE PROTHESES ARE FORMED BY SPRAYING WATER SOLUBLE AND WATER INSOLUBLE FIBERS ONTO A ROTATING MANDREL

The present application claims the benefit of priority from U.S. Provisional Application Ser. No. 60/048,091, filed May 30, 1997, incorporated herein by reference.

TECHNICAL FIELD

The present invention generally relates to porous prostheses and to methods of making the same. More particularly, the invention relates to porous prostheses and methods of making the same wherein the prostheses are formed by spraying fibers onto a rotating mandrel under conditions such that the resultant prostheses have a porous inner surface, more preferably both porous inner and outer surfaces.

BACKGROUND OF THE INVENTION

The use of generally tubular-shaped prostheses (also referred to as stents or grafts) to treat vascular disease or injury is well known. A typical treatment involves implanting a prosthesis to replace and/or repair portions of damaged or diseased blood vessels. Such prostheses have been formed from both natural and synthetic materials. As between natural and synthetic materials, much attention has been focused upon the development and use of acceptable synthetic prostheses formed from materials such as polymers or the like.

Current clinical practice relating to vascular prostheses has focused on the development and use of porous structures. Porous structures are currently preferred as such porous structures, after implantation in a host, tend to become covered with a lining of thrombus. Thus, the surface of the structure exposed to blood flow i.e., the flow surface, becomes less thrombogenic over time. Accordingly, synthetic prostheses desirably exhibit a certain amount of porosity effective to help promote tissue ingrowth that results in the formation of a lining of thrombus. Porosity is desirable on both the inner and outer surfaces of a prosthesis, but is particularly desirable on the inner, or flow, surface.

The quality and quantity of the porosity of the inner surface of a synthetic prosthesis is highly dependent upon the manner in which the prosthesis is made. For example, some synthetic prostheses have been made from compositions comprising a biocompatible, water insoluble elastomeric resin and a water soluble salt. After a prosthesis is formed from such a composition, the salt is rinsed out using hot water. The voids in the prosthesis formerly occupied by the salt contribute to the porosity of the inner wall of the prosthesis. This approach has a number of drawbacks, however. First, the resultant pore shape tends to correspond to the crystalline shape of the salt, and therefore tends to have sharp edges and corners. These sharp edges and corners can act like stress concentrators from which stresses are easily propagated. This has a negative impact upon the mechanical strength of the prosthesis. Further, a relatively high concentration of salt is generally required to achieve desired levels of porosity, which also can result in a mechanically weak prosthesis.

Synthetic prostheses with some porosity have also been prepared using the so-called continuous fiber winding technique. According to this technique, a polymer melt, solution, or dispersion is extruded through a fine orifice to form a polymeric fiber. The resultant polymeric fiber is then continuously wound onto a rotating mandrel. The circumferential velocity of the mandrel is generally higher than the velocity by which the fiber is extruded so that considerable stretching of the fiber takes place during winding. Because the fiber is still hot (melt processing) or still contains solvent (solution processing) when it reaches the mandrel, fiber-fiber binding takes place. After a number of passes, the desired thickness is reached. The fibrous structure may then be dried, cured, cooled, and removed from the mandrel. A porous, stable tube can result. The use of such a continuous fiber winding technique to form a porous prosthesis has been described in Leidner et al., "A Novel Process for the Manufacturing of Porous Grafts: Process Description and Product Evaluation," J. of Biomedical Materials Res., Vol. 17, No. 2, March 1983, pp. 229–247, incorporated herein by reference.

Advantageously, the use of continuous fiber winding provides a prosthesis with a fibrous structure, which is very desirable in terms of performance (e.g. tissue ingrowth) and mechanical properties such as strength, compliance, flexibility, and the like. Unfortunately, continuous fiber winding techniques may only be used in connection with polymeric materials that are spinnable, e.g., good fiber formers. Yet, there are a host of polymer materials without such good fiber forming characteristics that nonetheless have other characteristics that are extremely desirable in the manufacture and subsequent use of prostheses. For example, silicone resins are a class of materials that are desirable in terms of strength, compliance, flexibility, biocompatibility, elasticity, and the like, but are not spinnable fiber formers. Consequently, silicone resins and similar materials generally are not compatible with the continuous fiber winding technique.

Electrostatic spraying is a technique that may be used to form a fibrous prostheses from a wide range of polymer materials, (including polymers such as silicone resins) that are otherwise poor fiber formers. According to this technique, a polymer melt, solution, or dispersion is extruded through a fine orifice and directed toward a rotating mandrel. A voltage is maintained between the orifice and mandrel so that the polymer material is attracted electrostatically to the mandrel. In practice, droplets of the polymer material extruded from the orifice are electrostatically pulled toward the mandrel. The mandrel is thus struck with a plurality of short polymeric fibers that eventually coat the mandrel. A desired thickness of material can be built up, after which the resultant prosthesis can be dried, cured, cooled, and removed from the mandrel.

Unfortunately, the conventional electrostatic spraying technique suffers from some drawbacks. In particular, the short polymeric fibers tend to coalesce after striking the mandrel, at least to some degree. This causes the inner wall of the resultant prosthesis to have low, if any, porosity. Silicone fibers, in particular, tend to coalesce when electrostatically sprayed onto a mandrel to such a degree that the inner wall of the prosthesis is substantially smooth. Thus, prosthesis produced by the electrostatic spraying of silicone tend to lack the degree of porosity that would facilitate the desired ingrowth of host tissue.

Accordingly, there is a need for an approach by which prostheses can be electrostatically sprayed from polymeric materials, particularly silicone fibers and other polymers that are poor fiber formers, in such a way that the prostheses have a beneficial degree of porosity on the inner wall surfaces.

SUMMARY OF THE INVENTION

The present invention has resulted, at least in part, from the discovery that a fibrous, synthetic prosthesis with at least inner wall porosity can be formed on a suitable mold (preferably a rotating mandrel) by electrostatically spraying at least one water insoluble, polymeric fibrous component and at least one, separate water soluble fibrous component onto the mandrel to form a tubular prosthesis. As the tubular prosthesis is being formed, the fibrous components may be electrostatically sprayed onto the mandrel until the tubular prosthesis has the desired wall thickness. Electrostatic spraying may then be stopped, after which the fibrous component(s) may be dried, solidified, and/or cured (as appropriate depending upon how the fibrous components are to be provided). The water soluble fibrous component then may be washed out of, i.e., eluted from, the tubular prosthesis using an appropriate solvent, such as hot water. Elution leaves fibrous shaped voids in the tubular structure that provide the resultant prosthesis with the desired porosity.

Advantageously, the amount of porosity, the location of the porosity, and the mechanical properties of the resultant prosthesis are easy to control merely by varying easily adjusted parameters in the electrostatic spraying process such as the rotational speed of the mandrel, the flow rate of the sprayed materials onto the mandrel, the temperature at which the fibrous components are wound onto the mandrel, the solids content of polymer solutions used to form the fibers in embodiments using polymer solutions, combinations of these, and the like. Further, this approach provides a prosthesis with not only a fibrous physical structure provided by the water insoluble fibrous component, but also a fibrous porosity structure resulting from elution of the water soluble fiber component. Both fibrous features contribute to the mechanical strength of the prosthesis. Moreover, unlike conventional prostheses formed from salt-containing compositions that leave sharp edged pores that act like stress concentrators, the "fibrous" porosity characteristics of the present invention generally benefit from substantially less stress concentrating features.

While not wishing to be bound by theory, it is believed that the method of the present invention effectively produces a porous prosthesis due to the utilization of a water soluble fibrous component in combination with a water insoluble fibrous component. Specifically, it is believed that the water soluble fibrous component, being insoluble in the water insoluble fibrous component, acts as a physical spacer and helps to prevent and/or at least substantially reduce fiber coalescence that might otherwise occur in the absence of the water soluble fibers.

Accordingly, in one aspect, the present invention relates to a method of forming a porous, tubular, synthetic prosthesis. A prosthesis precursor comprising a water insoluble, fibrous component and a water soluble, fibrous component. At least a portion of the water soluble fibrous component is removed from the precursor.

Another aspect of the present invention relates to a prosthesis comprising a tubular body having an inner wall surface and an outer wall surface. The body comprises a fibrous, elastomeric, polymer structure and a fibrous porous structure.

In another aspect, the present invention relates to a method of making a tubular prosthesis precursor. A water insoluble fibrous component and a water soluble fibrous component are co-sprayed onto a mold to form the tubular prosthesis precursor comprising the water soluble fibrous component and a water insoluble fibrous component.

Another aspect of the present invention relates to a prosthesis precursor comprising a tubular body comprising a water insoluble fibrous component and a water soluble component.

BRIEF DESCRIPTION OF THE DRAWINGS

The above mentioned and other advantages of the present invention, and the manner of attaining them, will become more apparent and the invention itself will be better understood by reference to the following description of the embodiments of the invention taken in conjunction with the accompanying drawings wherein:

FIG. 3b is a side view of the housing of FIG. 3a;

FIG. 4b is a side view of the cover of FIG. 4a;

DETAILED DESCRIPTION OF THE INVENTION

The embodiments of the present invention described below are not intended to be exhaustive or to limit the invention to the precise forms disclosed in the following detailed description. Rather the embodiments are chosen and described so that others skilled in the art may appreciate and understand the principles and practices of the present invention. Accordingly, while the present invention will be described for the most part with specific reference to a vascular graft, the present invention is not intended to be so limited, but rather, the principles of the prevent invention may be applied to any implantable prosthetic device.

Figure 1:
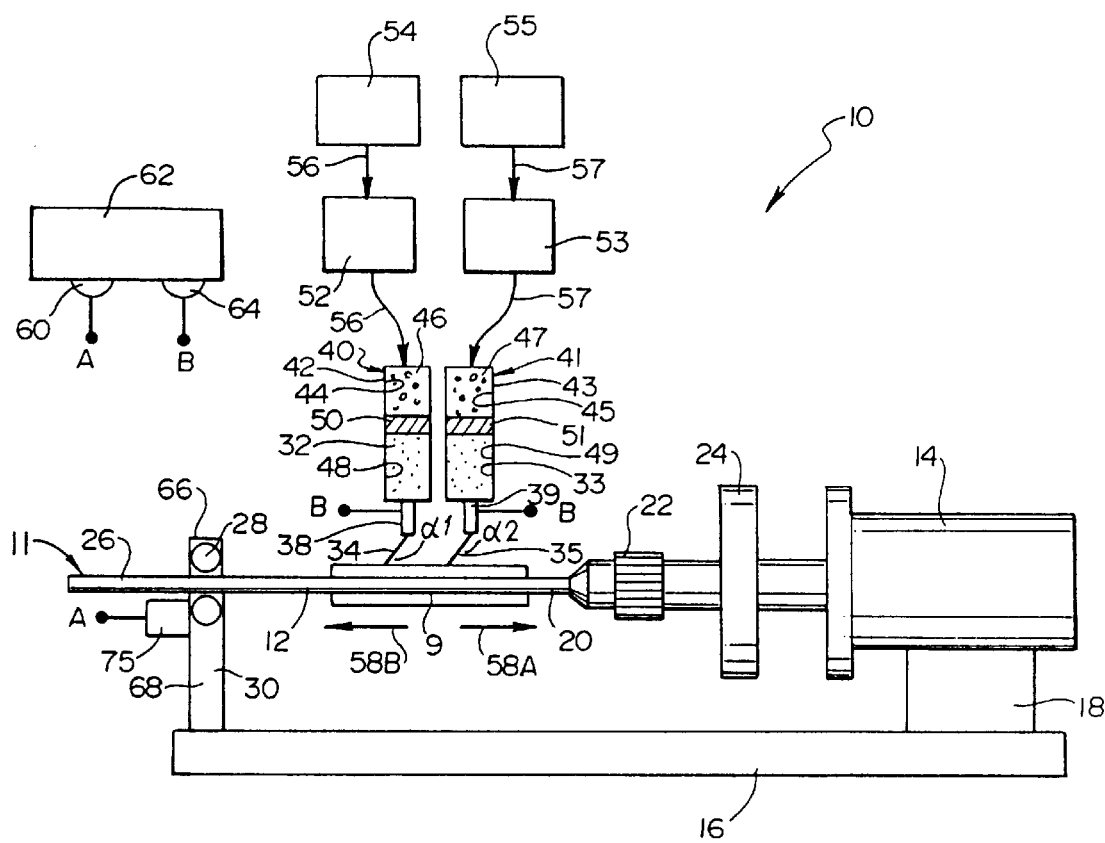
FIG. 1 is a schematic side view of an electrostatic spraying system suitable for making prostheses of the present invention.

FIG. 1 illustrates a particularly preferred approach in which the principles of the present invention may be practiced to form prosthesis 9. As an overview, this approach involves electrostatically co-spraying water insoluble, fiber forming composition 32 and a separate water soluble fiber forming composition 33 around a prosthesis mold, e.g. rotating mandrel 12. At this point in the manufacturing process, the resultant prosthesis 9 will thus comprise water insoluble fibrous component 34 and water soluble fibrous component 35, keeping in mind that portions of the solvents (if any) originally in these components at the time of spraying may not be present in prosthesis 9 due to volatilization. Because water soluble fibrous component 35 acts like a spacer between windings of water insoluble fibrous component 34, the presence of water soluble fibrous component 35 helps to prevent coalescence of water insoluble fibrous component 34. After spraying operations are completed, and optionally after water insoluble fiber component 34 is dried and/or cured, the water soluble fiber component 35 is easily removed from prosthesis 9 by washing the prosthesis with water or any similar eluent. Advantageously, this leaves voids in the spaces formerly occupied by water soluble fibrous component 35, thus providing prosthesis 9 with a substantially higher level of porosity than would result if no water soluble fibrous component 35 were to have been co-sprayed with water insoluble fibrous component 34.

In more detail now, FIG. 1 shows electrostatic spraying device 10 that includes mandrel assembly 11 including a prosthesis mold in the form of rotating mandrel 12. Mandrel 12 is rotatably driven by motor 14, which is mounted to base 16 upon motor support 18. Preferably, the rotational output of motor 14 is controllably variable so that the rotational speed of mandrel 12 can be adjusted as desired. One end 20 of mandrel 12 is gripped in the jaws of chuck 22, which in turn is operationally mounted to motor 14 by coupler 24. The opposite end 26 of mandrel 12 is rotatably journalled in bearings 28 supported in mandrel support 30. The exterior diameter of mandrel 12 will determine the inner diameter size of prosthesis 9. Device 10 is configured, therefore, so that mandrel 12 is easily removed and replaced with a mandrel having a different diameter, allowing prosthesis 9 to be formed with any desired inner diameter within a wide size range merely be choosing and inserting an appropriately sized mandrel into device 10.

In typical applications, fiber diameter of each of fiber components 34 and 35 typically is independently in the range from 10 micrometers to 100 micrometers, preferably 20 micrometers to 50 micrometers, and mandrel rotational speed typically is in the range from about 200 rpm to about 2200 rpm, preferably 1500 rpm to 2000 rpm. The corresponding average pore size typically will be in the range from about 10 micrometers to about 200 micrometers, preferably from about 20 micrometers to about 80 micrometers, more preferably about 30 micrometers for vascular application.

Water insoluble fibrous component 34 is formed by extruding water insoluble fiber forming composition 32 from fiber forming subassembly 40, and water-soluble fibrous component 35 is formed by extruding water soluble fiber forming composition 33 from fiber forming subassembly 41. Fiber forming subassemblies 40 and 41 respectively comprise cylinders 42 and 43 in which hydraulic fluid chambers 44 and 45 are separated from fiber forming composition chambers 48 and 49 by plungers 50 and 51. Chambers 44 and 45 are filled with hydraulic fluid 46 and 47 and fiber forming composition chambers 48 and 49 are filled with fiber forming compositions 32 and 33. Needles 38 and 39 are in fluid communication with chambers 48 and 49 and provide orifices through which fiber forming compositions 32 and 33 may be extruded to form fibrous components 34 and 35 as a consequence of pressure developed by downward movement of plungers 50 and 51. Needles 38 and 39 generally are independently formed from a conductive material to facilitate the use of the electrostatic spraying technique when forming prosthesis 9, and may be of any suitable shapes and sizes. For example, each of needles 38 and 39 may be 23 to 25 gauge in size and may have a length of 3 cm. The distance between needles 38 and 39 is not critical. However, less material from fiber forming compositions 32 and 33 is wasted with each pass as the needle spacing is reduced. In typical applications, such spacing may range from about 1 mm to about 4 cm, preferably from about 1 cm to about 2 cm.

Plungers 50 and 51 are forced downward to carry out extrusion when volumetric pumps 52 and 53 motivate hydraulic fluid 46 and 47 from fluid sources 54 and 55 into chambers 44 and 45 via supply lines 56 and 57. Hydraulic fluids 46 and 47 may be any suitable hydraulic gas or liquid, although a liquid, such as an alcohol, is presently preferred. Desirably, the rate at which pumps 52 and 53 motivate hydraulic fluids 46 and 47 into chambers 44 and 45 is independently controllable so that the rates of extrusion of fiber forming compositions 32 and 33 can be adjusted over a wide operating range. The particular rates at which volumetric pumps 52 and 53 motivate hydraulic fluids 46 and 47 into chambers 44 and 45 may thus be varied depending on the nature of the fiber forming composition 32 and 33. For example, when fiber forming composition 32 comprises 20 parts by weight of a silicone resin and 80 parts by weight of solvent, rates of extrusion in the range of from about 0.1 ml/min to about 0.6 ml/min have been found to be suitable. The desired extrusion rate of fiber forming composition 33 relative to fiber forming composition 32 will be described in more detail below.

Cylinders 42 and 43 are supported upon fixture 80 (shown in FIGS. 3a, 3b, 4a and 4c). Fixture 80 further supports needles 38 and 39 at a suitable distance from mandrel 12 for carrying out fiber forming and spraying operations. In general, better fibers are formed as this distance is increased. However, if the distance is too great, fibrous component 34 may be too dry upon reaching mandrel 12, so that poor fiber-fiber bonding results. On the other hand, if the distance is too small, portions of fibrous component 34 may have a greater tendency to coalesce around mandrel 12. Generally, the optimum distance may be easily determined empirically for any one particular fiber forming composition 32 using routine testing procedures. As one example, when fiber forming composition 32 comprises about 20 to 30 parts by weight of a silicone resin and 80 parts by weight of solvent, a distance of 20 mm to 200 mm from needles 38 and 39 to mandrel 12 has been found to be suitable. Greater distances are preferred so long as adequate fiber-fiber bonding is achieved.

Needles 38 and 39 move axially back and forth relative to mandrel 12 so that prosthesis 9 is formed along a length of mandrel 12. This relative axial movement of needle 38 is represented schematically by arrow 58a in FIG. 1, which shows needles 38 and 39 moving to the right relative to mandrel 12. In the course of the next pass, and as shown by arrow 58b, needles 38 and 39 would move to the left relative to mandrel 12. With each pass, the thickness of prosthesis 9 is increased. Enough passes are made to provide prosthesis walls having the desired thickness for the prosthetic application in mind. The relative axial movement between needles 38 and 39 and mandrel 12 can be accomplished by causing actual axial movement of the needles 38 and 39 and/or mandrel 12. Preferably, however, needles 38 and 39 remain stationary while mandrel 12 is translated axially back and forth using any suitable translation device to accomplish such movement. Power for such movement can be provided by motor 14 or by another power source (not shown) if desired. The speed of axial movement may be in the range effective to provide angles $_1$, and $_2$ of from about 10° to about 85°, preferably about 45° between the sprayed material and mandrel 12. A typical translational speed, for example, is about 400 cm/min.

The electrostatic spraying technique involves extruding fiber components 34 and 35 from needles 38 and 39 under conditions such that fibrous components 34 and 35 are electrostatically attracted to mandrel 12 during spraying operations. This is accomplished by developing a voltage between needles 38 and 39 and mandrel 12 by electrically coupling high voltage terminal 60 of power source 62 to mandrel 12 and low voltage terminal 64 to needles 38 and 39. Of course, it is also possible to electrically couple high voltage terminal 60 of power source 62 to needles 38 and 39 and low voltage terminal 64 to mandrel 12, if desired. Generally, the attraction between mandrel 12 and fibrous components 34 and 35 increases as the voltage between mandrel 12 and needles 38 and 39 is increased. To maximize this attraction, therefore, it is generally desirable to use as high a voltage as practical, so long as sparking is avoided. As suggested guidelines, using a voltage in the range of 10 kV to about 45 kV would be suitable, with higher voltages being more suitable as the distance from mandrel 12 to needles 38 and 39 is increased.

Figure 2:
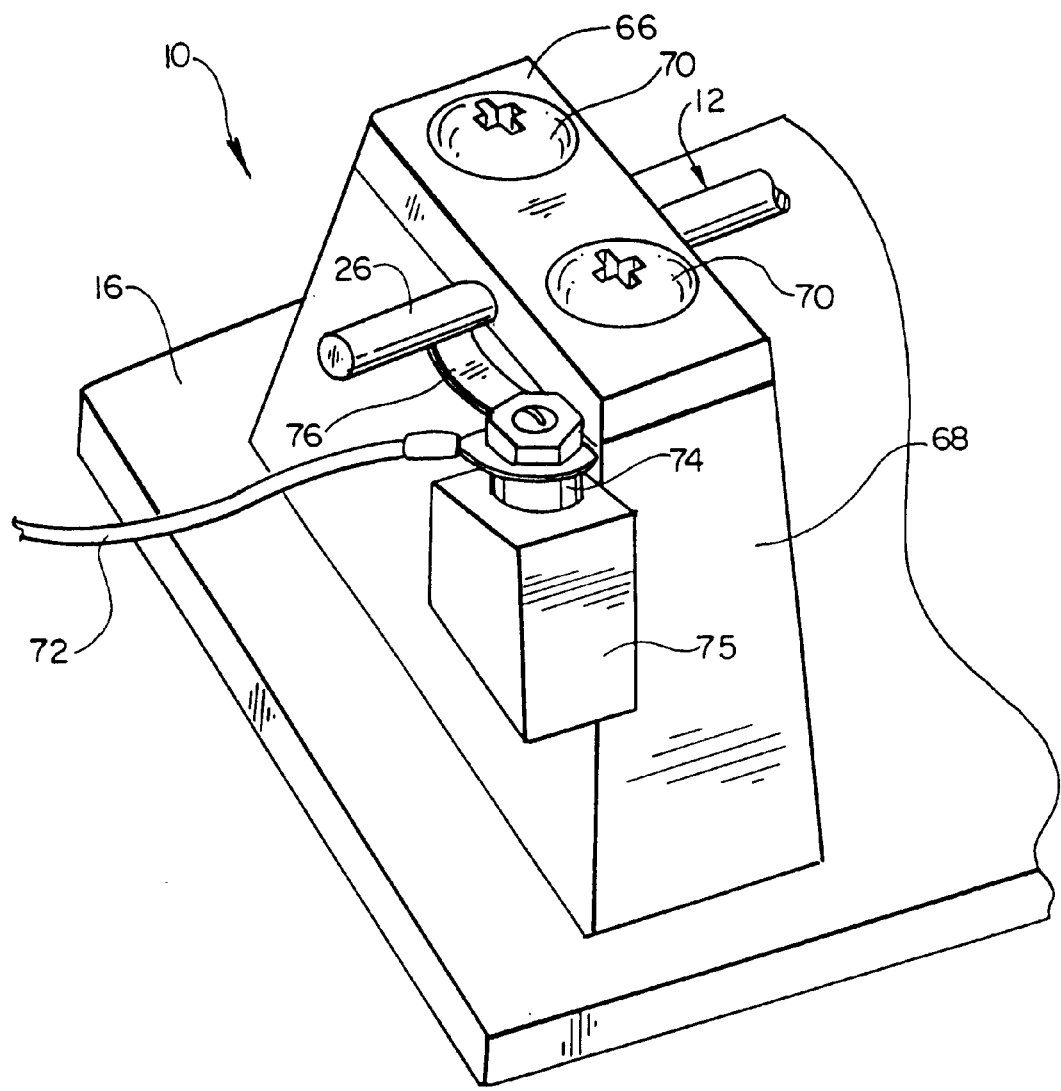
FIG. 2 is a close-up perspective view of a portion of the system of FIG. 1 showing the electrical connection between a power source and the rotating mandrel in more detail.
Figure 3A:
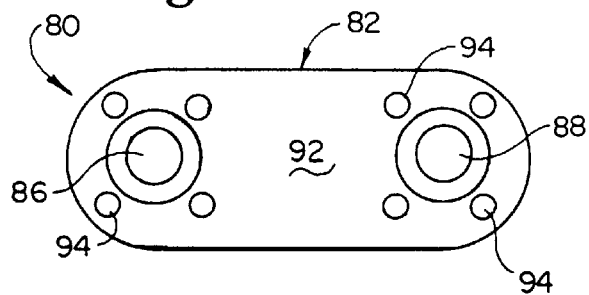
FIG. 3a is a top view of the housing of a fixture used for supporting cylinders 42 and 43 of FIG. 1.
Figure 3B:
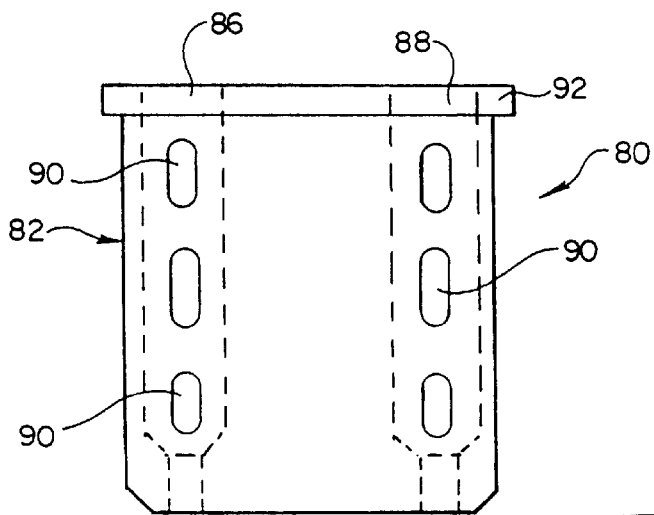

FIG. 2 shows the coupling between power source 62 and mandrel 12 in more detail. Specifically, FIG. 2 shows a portion of end 26 of mandrel 12 projecting from mandrel support 30. As shown, mandrel support 30 includes top 66 releasably secured to bottom 68 by screws 70. Top 66 can thus be removed from bottom 68 in order to remove and replace mandrel 12. Mandrel support 30 also includes block 75 attached to bottom 68. Wire 72 from power source 62 (FIG. 1) is connected to terminal 74. Terminal 74, in turn, is electrically coupled to mandrel 12 by resilient metal strip 76.

Referring again to FIG. 1, the high voltage developed between needles 38 and 39 and mandrel 12 makes it important to observe some safety precautions. Firstly, mandrel 12 and needles 38 and 39 are desirably electrically isolated from motor 14 as well as the environment. Accordingly, base 16, supports 18 and 30, and coupler 24 are desirably formed of a structurally sound, insulating, polymeric material. Fixture 80 may also include similar materials (not shown) in similar fashion. A wide range of polymers may be used for this insulating purpose, including one or more polyurethanes, polyacetals, polyamides, polyimides, epoxy resins, phenolic resins, combinations of these, and the like. In preferred embodiments, the insulating polymer is a polyacetal commercially available from E. I DuPont de Nemours & Co. under the tradename DELRYN.

Additional precautions may also be taken to ensure safe operation of device electrostatic spraying 10. For example, portions of electrostatic spraying device 10, including mandrel assembly 11 and cylinders 42 and 43, may be housed in an insulative enclosure (not shown) having a door (not shown) equipped with a safety interlock that disables power source 62 when the door is open. Additionally, the door may be fitted with a clear, insulating plastic panel allowing operations to be observed but offering further protection against the voltage developed by power source 62. Finally, power source 62, pumps 52 and 53, and motor speed controls (not shown) can be installed outside of the enclosure so that the operator does not have to open the door to the enclosure to gain access to these devices.

Fiber forming composition 32 preferably may be any extrudable composition comprising a biocompatible, water insoluble, thermoplastic or thermosetting, elastomeric polymer or combination of polymers from which fiber component 34 may be formed and then electrostatically sprayed around mandrel 12. Preferred elastomeric polymers have an elongation at break of at least 200%, preferably from about 200% to about 800% and have a longitudinal tensile force at break in the range of 1 kg/cm$^2$ to 17 kg/cm$^2$. It is further preferred that the elastomeric polymers utilized as fiber forming composition 32 have tensile characteristics so that the resultant prosthesis 9 preferably has a radial tensile force at break in the range of 1 kg/cm$^2$ to 20 kg/cm$^2$.

Representative examples of elastomeric polymers suitable for use in fiber forming composition 32 include silicone, high density polyethylene, polyethylene terephthalate, polyurethane, polyamide, polyester, polyorthoester, polyanhydride, polyether sulfone, polycarbonate, polypropylene, polytetrafluoroethylene, combinations of these, or the like. Of these, a thermosetting silicone resin is preferred. One specific example of a suitable silicone resin is commercially available under the trade designation 40000 from Applied Silicone Corp. When cured per the guidelines provided by the vendor (1 hour at 150° C.), this resin has a durometer hardness, Shore A units, of 35, a tensile strength of 1800 psi, and an elongation at break of about 800%. This polymer may be obtained as a 35% solids solution in xylene, or more preferably as a 29% solids solution in trichloroethane. Another example of a suitable silicone resin is commercially available under the trade designation MED-4865 from NuSil Silicone Technology. When cured per the guidelines provided by the vendor (10 minutes at 180° C.), this resin has a durometer hardness, Shore A units, of 65, a tensile strength of 1200 psi, and an elongation at break of about 500%. This polymer may be obtained "neat", i.e., at 100% solids.

Optionally, fiber forming composition 32 may further comprise one or more optional therapeutic ingredients such as anticoagulants, thrombolytics, steroids, vasodilators, antimicrobials or antibiotics, antimitotics, antiproliferatives, antisecretory agents, non-steroidal anti-inflammatory drugs, immunosuppressive agents, growth factor antagonists, free radical scavengers, antioxidants, biologic agents, radiotherapeutic agents, radiopaque agents and radiolabelled agents, combinations of these, and the like in accordance with conventional practices.

Fiber forming composition 32 preferably is in an extrudable fluid form such as a melt, a solution, or a dispersion. More preferably, fiber forming composition 32 is a solution or dispersion comprising one or more water insoluble polymers as described above dissolved (solution) or dispersed (dispersion) in a suitable organic solvent. Fiber forming composition 32 should comprise a sufficient amount of solvent so that fiber forming composition 32 has an appropriate viscosity to carry out extrusion and fiber forming operations. As general guidelines, fiber forming composition 32 may comprise about 80 parts by weight of solvent per 10 to 160 parts by weight of polymer. In a particularly preferred embodiment of the invention, fiber forming composition 32 comprises 20 parts by weight of a silicone resin and 80 parts by weight of solvent.

A wide variety of solvents or combination of solvents may be incorporated into fiber forming composition 32. The type of solvent utilized will depend upon a number of factors, such as the type of polymer being used, the desired solvent drying rate, the temperature at which operations are carried out, and the like. Additionally, the solvent utilized should have a drying rate so that the fibers are not too wet or too dry at the time of striking mandrel 12. If the solvent evaporates too quickly i.e., the fibers are too dry, poor fiber-fiber bonding may result. If the solvent evaporates too slowly, i.e., the fibers are too wet, the fibers will have a greater tendency to coalesce together. The resultant prosthesis may have low or no, porosity. In some instances, an otherwise suitable solvent having a less than optimum drying rate can be accommodated by adjusting the distance between needle 38 and mandrel 12. For example, if the solvent dries relatively slowly, increasing the distance from needle 38 to mandrel 12 will provide the solvent with more time to evaporate so that the fibers are not too wet. If the solvent dries too quickly, reducing the distance from needle 38 to mandrel 12 will reduce the amount of time the solvent has to dry so that the fibers are not too dry.

In preferred embodiments of the present invention in which fiber forming composition 32 comprises a silicone resin, the solvent preferably comprises one or more halogenated alkanes. Preferred halogenated alkanes include a trihaloethane such as trichloroethane, a dihaloethane such as dichloroethane, a trihalomethane such as trichloromethane, a dihalomethane such as dichloromethane, combinations of these, and the like.

In a preferred embodiment, the solvent of fiber forming composition 32 comprises a first solvent component of relatively high volatility (i.e., a relatively high boiling point) and a second solvent component with relatively low volatility (i.e., a relatively low boiling point). The use of first and second solvent components provides a beneficial viscosity change during processing. Initially, at the time of extruding through needle 38, fiber forming composition 32 desirably has a relatively low viscosity (generally corresponding to a higher solvent content). However, after leaving needle 38, the viscosity of fiber forming composition 32 desirably increases rapidly (generally corresponding to a lower solvent content) to facilitate effective coating. Accordingly, fiber forming composition 32 desirably includes enough of the first and second solvent components so that fiber forming composition 32 is conveniently extrudable through needle 38. After leaving needle 38, the more volatile first solvent component rapidly dries, leaving a reduced amount of solvent, and hence a higher viscosity.

Preferably, the first solvent component has a boiling point that is at least 10° C. greater, preferably at least 25° C. greater, more preferably from about 25° C. to about 50° C. greater, than that of the second solvent component. If a combination of solvents is used, it is preferred that the weight ratio of the second solvent component to the first solvent component is in the range from 2:1 to 10:1, preferably 3:1 to 5:1. When fiber forming composition 32 comprises a silicone resin, a particularly preferred first solvent component is trichloroethane (boiling point of 74.1° C.) and a particularly preferred second solvent component is dichloromethane (boiling point of 47.1° C.).

Fiber forming composition 33 preferably is in an extrudable fluid form such as a melt, a solution, or dispersion comprising a water soluble, thermoplastic, elastomeric material capable of being extruded and electrostatically sprayed onto mandrel 12. The mechanical and fiber forming characteristics of fiber forming composition 33 are not critical. However, it is important that fiber forming composition 33 reach and stay on mandrel 12 so that the fibers of fiber component 35 act as spacers among the fibers of fiber component 34. More preferably, fiber forming composition 33 is a dispersion or solution comprising the water soluble, oligomer and/or polymer and a sufficient amount of a solvent to provide composition 33 with a suitable extrudable viscosity. As general guidelines, fiber forming composition 33 may comprise 0 to 60 parts by weight of solvent per 10 to 160 parts by weight of the water soluble, fiber forming material.

A wide variety of water soluble oligomers and polymers are known and any of these can be incorporated singly or in combination into fiber forming composition 33. Examples of such hydrophilic materials include polyethylene glycol (PEG) preferably having a weight average molecular weight in the range from 1000 to about 10,000 (preferably 8000); polyvinyl alcohol; polyacrylamide; poly(methylvinyl ether); polyacrylic acid; poly(vinylpyridine); esters of poly(meth) acrylic acid wherein the ester group may be represented by the formula—OR in which the R moiety is sufficiently small (e.g., methyl or ethyl or other C1 or C2 type of moiety) so that the polymer is water soluble; similar esters of polyvinyl alcohol; combinations of these, and the like. Most preferably, the water soluble material is PEG, more preferably PEG having a weight average molecular weight of about 8000.

A wide variety of solvents may be incorporated into fiber forming composition 33 with beneficial results. The particular type of solvent used will depend upon a number of factors, such as the degree of hydrophilicity of the water soluble material, the temperature of fiber forming composition 33 at the time of extrusion and spraying, the desired drying rate of the solvent so that the water soluble fiber is not too dry or too wet when being sprayed around mandrel 12, and the like. Representative examples of suitable solvents in which to dissolve or disperse fiber forming composition 33 include water, alcohol, combinations of these, and the like.

The porosity of prosthesis 9 is greatly dependent upon the amount of water soluble fibrous component 35 relative to the amount of water insoluble fibrous component 34 incorporated into prosthesis 9. Generally, porosity increases as the relative amount of water soluble fibrous component 35 increases. Accordingly, if the amount of water soluble fibrous component 35 incorporated into prosthesis 9 is too low, the porosity of prosthesis 9 may be too low as well. On the other hand, if too much of water soluble fibrous component 35 is incorporated into prosthesis 9, the level of porosity could be so high as to unduly adversely impact the mechanical properties of prosthesis 9. Balancing these concerns, it is preferred that prosthesis 9 include 50 to 75 parts by weight of water soluble fibrous component 35 per 25 to 50 parts by weight of water insoluble fibrous component 34. In determining the relative parts by weight of fibrous component 35 and 34 incorporated into prosthesis 9, the solvent incorporated into each component is not included in the calculation.

The relative amount of fibrous components 34 and 35 incorporated into prosthesis 9 is generally equal to the relative mass flow rate, not including solvent, at which compositions 32 and 33 are extruded from needles 38 and 39. Thus, the desired content of prosthesis 9 (in terms of the relative amounts of fiber components 34 and 35) can be established by operating pumps 52 and 53 so as to extrude compositions 32 and 33 at the corresponding relative mass flow rates. For example, in preferred embodiments of the invention, it may be desirable to incorporate 30 parts by weight of water insoluble fibrous component 34 and 70 parts by weight of water soluble fibrous component 35 into prosthesis 9 under conditions wherein fibrous composition 32 is extruded at a mass flow rate of 0.3 g/min. To ensure that the desired amount of water soluble fibrous component 35 is present, then, fibrous composition 33 would be extruded at a mass flow rate of 0.7 g/min.

Figure 4A:
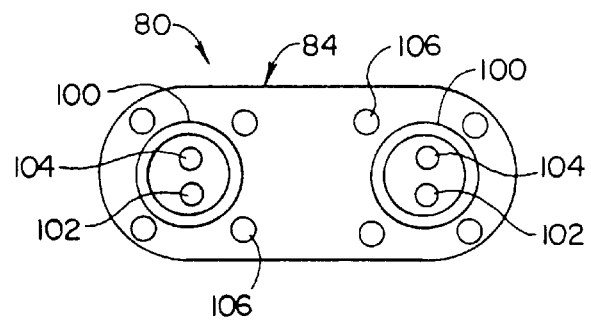
FIG. 4a is a top view of a cover that fits over the housing of FIGS. 3a and 3b.
Figure 4B:
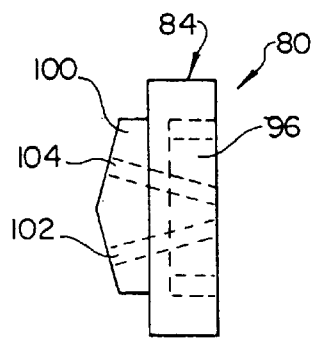

FIGS. 3A, 3B, 4A, and 4B show a preferred embodiment of fixture 80 effective for supporting cylinders 42 and 43 for use with electrostatic spraying device 10 of FIG. 1. Fixture 80 includes housing 82 (FIGS. 3A and 3B) and cover 84 (FIGS. 4A and 4B). Housing 82 includes first and second cavities 86 and 88 for receiving cylinders 42 and 43 (shown in FIG. 1), respectively. To provide a liquid and airtight seal between housing 82 and cover 84, an o-ring (not shown) may be positioned between cover 84 and housing 82 around each cavity 86 and 88. Housing 82 includes portals 90 to allow the fluid level in cylinders 42 and 43 to be visually monitored. Housing 82 further includes top flange 92 including bolt holes 94 for receiving bolts (not shown) to secure cover 84 in place over housing 82.

Cover 84 includes receptacles 96 (only one of which can be seen in FIG. 4b) for receiving the tops of cylinders 42 and 43 (FIG. 1), respectively. A cap portion 100 is provided over each receptacle 96. Each cap portion 100 includes an aperture 102 for receiving a supply line (not shown) through which hydraulic fluid is pumped into the corresponding cylinder. Each cap portion 100 also includes an aperture 104 for receiving a bleed tube (not shown) through which hydraulic fluid can be discharged from the corresponding cylinder. Bolt holes 106 cooperate with bolt holes 94 of housing 82 for receiving bolts (not shown) to secure cover 84 in place over housing 82. In use, cylinders 42 and 43 are first lowered into housing 82. Cover 84 is then positioned over housing 82 and bolted into place, thus securing cylinders 42 and 43 in housing 82.

One preferred method of operation for forming prosthesis 9 using electrostatic spraying device 10 will now be described. At the outset, chambers 48 and 49 of cylinders 42 and 43 are filled with fiber forming composition 32 and fiber forming composition 33, respectively. Motor 14 is turned on to rotatably drive mandrel 12 at the desired rotational speed, and power source 62 is turned on to establish the desired level of voltage difference between mandrel 12 and needles 38 and 39. In the meantime, mandrel assembly 11 is axially translated back and forth at a velocity relative to needles 38 and 39 so as to establish the desired angle at which fiber components 34 and 35 strike mandrel 12, e.g., approximately 45°. Pumps 52 and 53 are then actuated to extrude fiber forming compositions 32 and 33 through needles 38 and 39, respectively, at the desired mass flow rates. The resultant fibrous components 34 and 35 are electrostatically attracted to rotating mandrel 12. Fibrous components 34 and 35 coat mandrel 12 as a result. Mandrel 12 and prosthesis 9 may be heated during winding operations, if desired. For example, a 250 watt IR lamp can be placed about 190 mm away from mandrel 12 for this purpose.

The wall thickness of prosthesis 9 increases with each pass of mandrel 12 beneath needles 38 and 39. When prosthesis 9 has the desired thickness, spraying operations may be stopped. Advantageously, the fibers of water soluble fibrous component 35 function as spacers between the fibers of water insoluble fibrous component 34, helping to prevent coalescence that might otherwise occur. Water soluble fibrous component 35 may then be easily eluted from prosthesis 9 using a suitable eluent, such as hot water or the like. Elution can take place before or after drying and/or curing, but most preferably occurs after drying and curing of water insoluble fibrous component 34 so that fiber spacing is preserved as much as possible. After elution of water soluble fibrous component 35, the spaces formerly occupied by water soluble fibrous component 35 provide prosthesis 9 with the desired porosity. After elution, prosthesis 9 can be dried, sterilized, and then packaged and/or deployed for therapeutic use.

Co-spraying of fibrous components 34 and 35 may be carried throughout the entirety, or only one or more selected portions, of the spraying process. This flexibility allows the distribution of porosity characteristics within prosthesis 9 to be easily controlled. For example, co-spraying may occur throughout the entirety of winding operations if it is desired that prosthesis 9 have porosity distributed throughout its entirety. Alternatively, co-spraying may occur only at the beginning and/or ending portions of spraying operations if it is desired that prosthesis 9 have porosity only proximal to the inside and/or outside surfaces of prosthesis 9. Likewise, to provide porosity only within prosthesis 9, but not at the surfaces, co-spraying may occur only during a middle portion of spraying operations.

Figure 5:
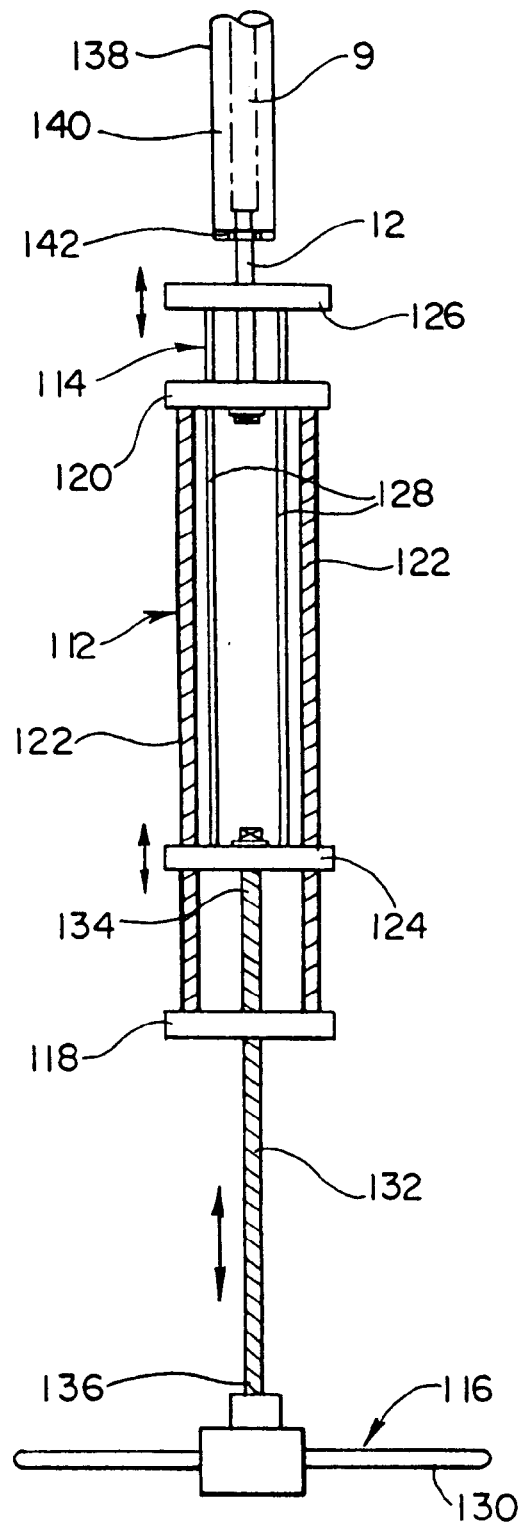
FIG. 5 is a schematic side view of a graft removal device suitable for removing a prostheses formed on the system of FIG. 1.

Once formed, prosthesis 9 may be removed from mandrel 12 using any suitable technique that does not damage prosthesis 9. For example, FIG. 5 shows a prosthesis removal device 110 effective for prosthesis removal. Prosthesis removal device 110 includes main frame 112, sliding carriage 114, and handle assembly 116. Main frame 112 includes stationary plates 118 and 120 supporting four rods 122 (only two of which can be seen) extending between stationary plates 118 and 120.

Sliding carriage 114 includes moving plates 124 and 126 connected to each other by four rods 128 (only two of which can be seen). Moving plate 124 is slideably mounted over rods 122 between stationary plates 118 and 120, while moving plate 126 is positioned outboard relative to stationary plate 120. Rods 128 slideably pass through stationary plate 120 so that sliding carriage 114 is moveable relative to main frame 112. Moving plate 126 and stationary plate 120 include cooperating apertures allowing mandrel 12 to be slideably inserted through moving plate 126 and then bolted or otherwise secured to stationary plate 120. In this way, mandrel 12 is fixedly secured relative to main frame 112, but sliding carriage 114 can be slideably moved toward (forward) or away from (backward) prosthesis 9 supported upon mandrel 12.

Handle assembly 116 includes handle 130 and threaded rod 132. At one end 134, threaded rod 132 is securely fastened to moving plate 124. At the other end 136, threaded rod 132 is coupled to handle 130. Threaded rod 132 also threadably engages stationary plate 118. Consequently, an operator can turn handle 130, which in turn causes threaded rod 132 to push moving plate 124, and hence sliding carriage 114, forward (toward stationary prosthesis 9) or backward (away from prosthesis 9).

According to one method of using graft removal device 110, prosthesis 9, while on mandrel 12, is placed into water in container 138. The water impregnates the pores of prosthesis 9. The water is frozen, whereby prosthesis 9 is firmly frozen and gripped in ice 140. With container 138 in place, mandrel 12 is inserted into graft removal device 110. The operator then turns handle 130 in order to drive sliding carriage 114 against container 138. An optional O-ring 142 is used to cushion the resultant force of moving plate 126 acting against container 138. By this action, container 138, ice 140, and prosthesis 9 are pushed off mandrel 12, leaving prosthesis 9 frozen in ice 140 in container 138. Because prosthesis 9 is encased in ice 140, prosthesis 9 is well protected. Prosthesis 9 is easily recovered for further processing, packaging, and/or use by melting ice 140.

After being formed, prosthesis 9 may optionally be seeded with cells such as endothelial cells, or with genetically engineered cells, and the like to limit thrombosis, neointimal hyperplasia and generally to increase the biocompatibility of the system. Similarly, the surfaces of the prostheses may be coated with agents such as fibronectin, laminum, glycoaminoglycans or other proteins to attract and adhere cells and cellular substances which may further enhance the hemocompatibility of prosthesis 9.

Figure 6:
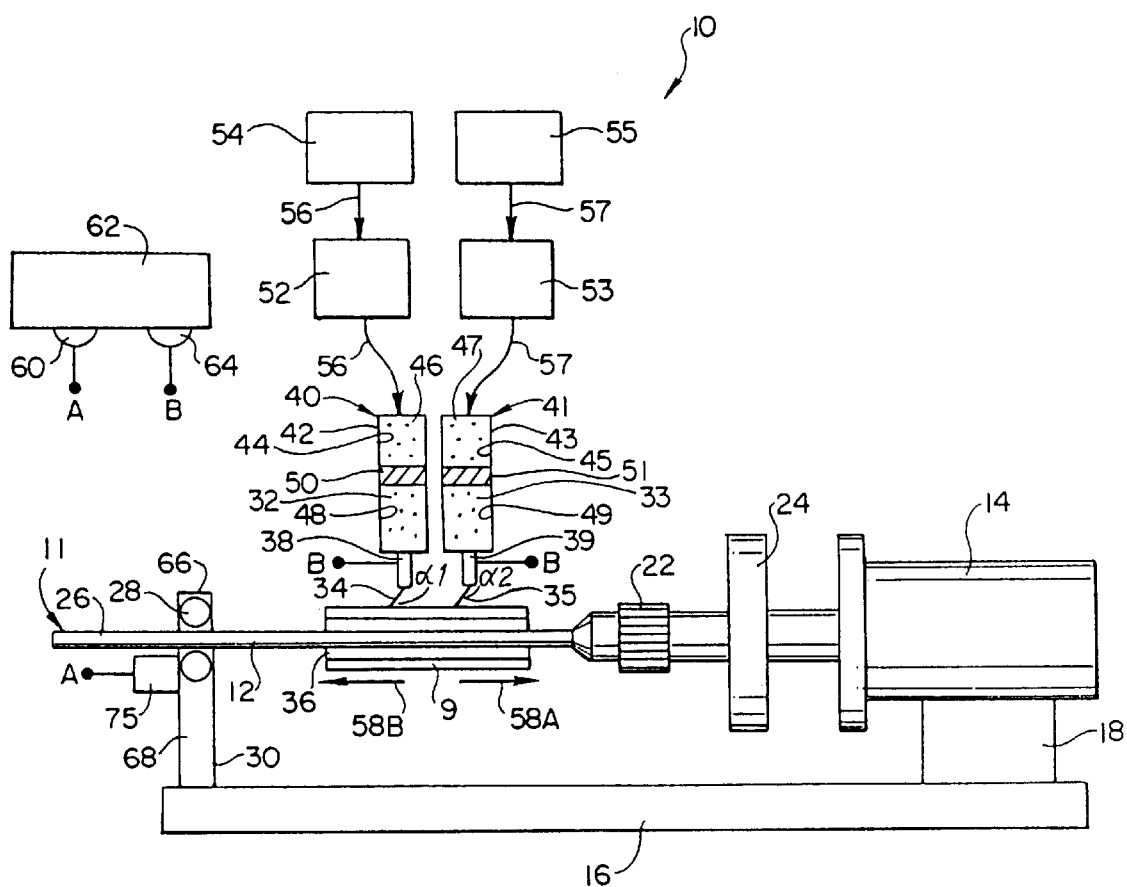
FIG. 6 is an alternative schematic side view of an electrostatic spraying system suitable for making prostheses of the present invention.
Figure 7:
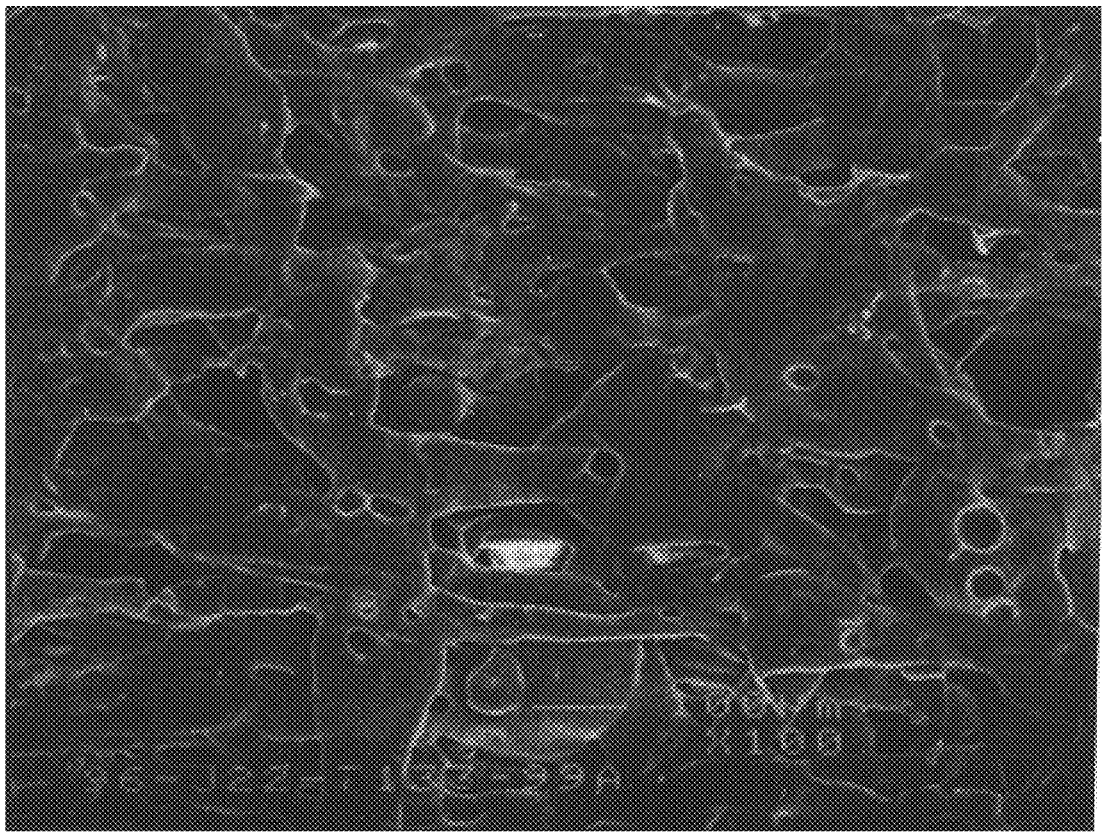
FIG. 7 is an SEM photograph at ×100 magnification of the inner surface of prosthesis sample 99-A of Example 1 that was formed by electrostatically co-spraying silicone fibers and fibers comprising liquid PEG having a molecular weight of 600 onto a rotating mandrel.
Figure 8:
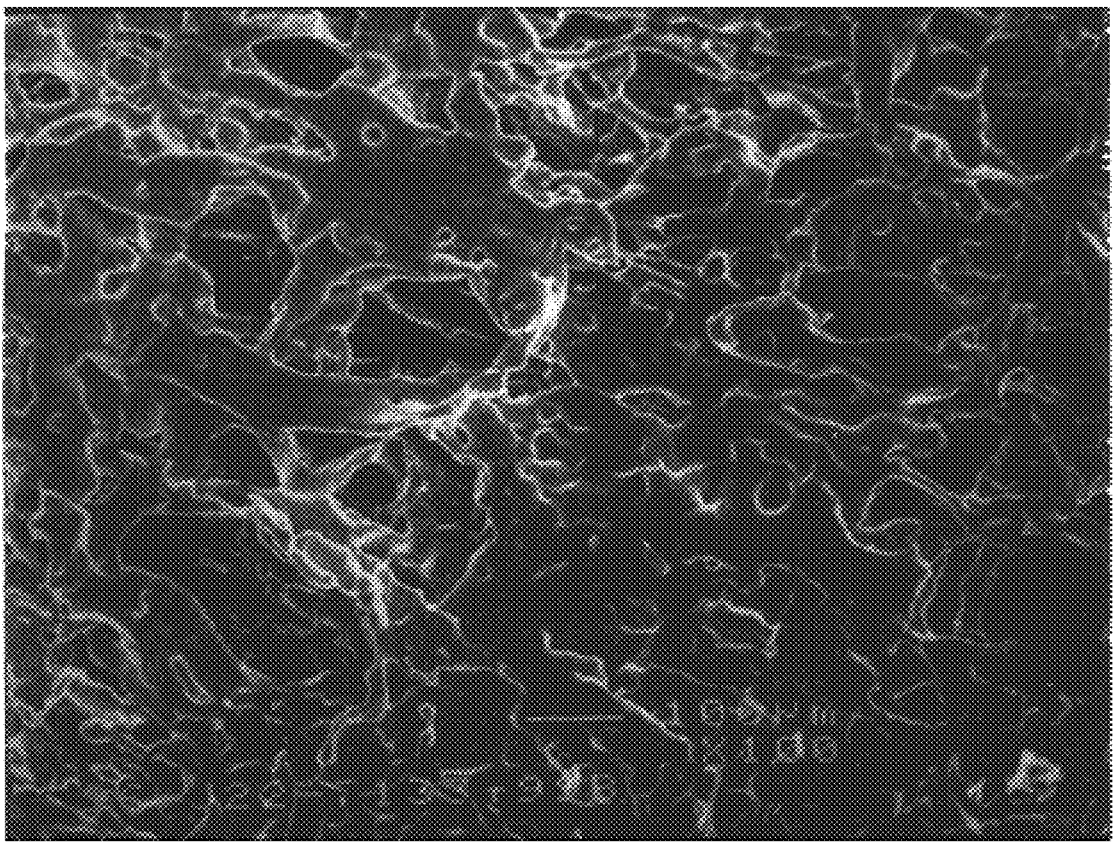
FIG. 8 is an SEM photograph at ×100 magnification of the inner surface of prosthesis sample 99-B of Example 1 that was formed by electrostatically co-spraying silicone fibers and fibers comprising solid PEG having a molecular weight of 8000 onto a rotating mandrel.
Figure 9:
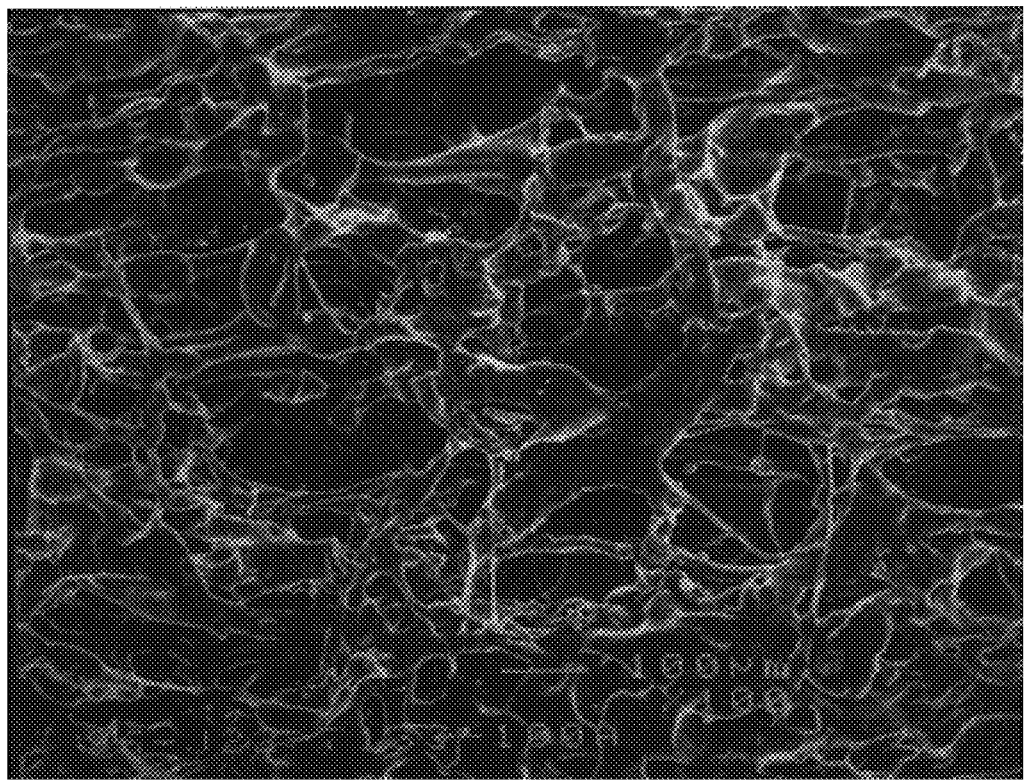
FIG. 9 is an SEM photograph at ×100 magnification of the inner surface of prosthesis sample 100-A of Example 1 that was formed by electrostatically co-spraying silicone fibers and fibers comprising solid PEG having a molecular weight of 8000 onto a rotating mandrel.
Figure 10:
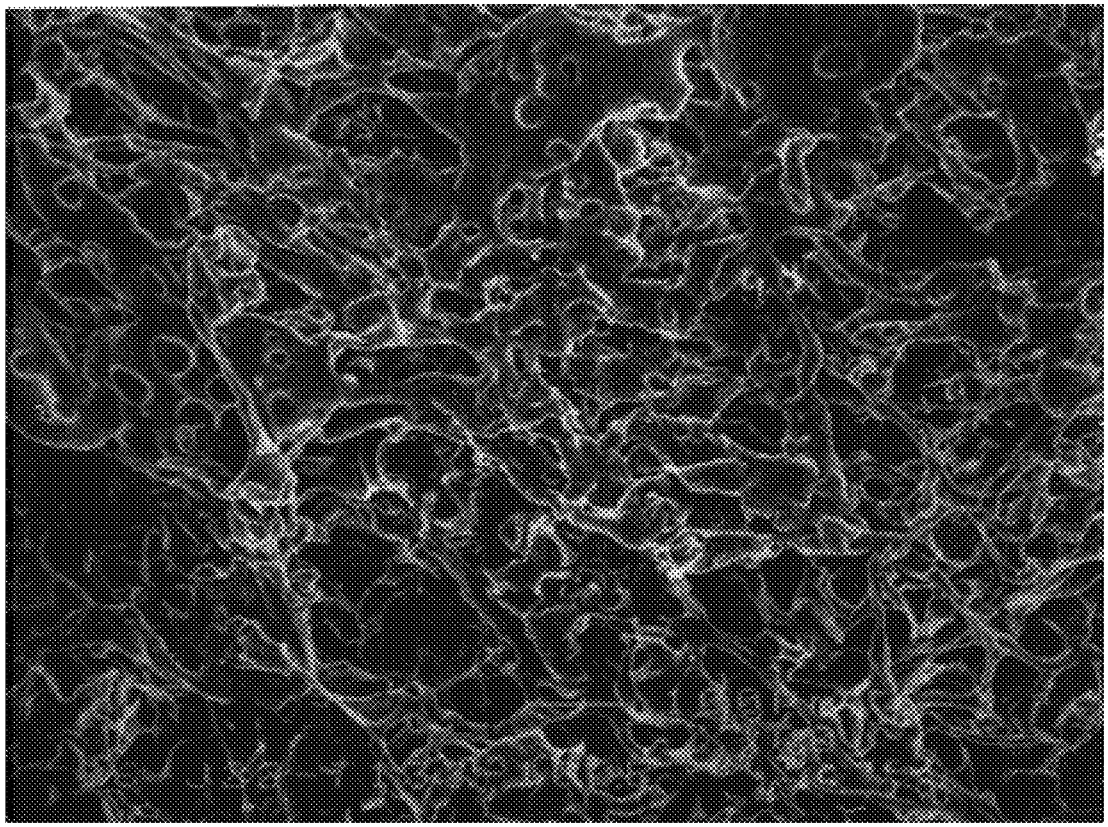
FIG. 10 is an SEM photograph at ×100 magnification of the inner surface of prosthesis sample 100-B of Example 1 that was formed by electrostatically co-spraying silicone fibers and fibers comprising solid PEG having a molecular weight of 8000 onto a rotating mandrel.
Figure 11:
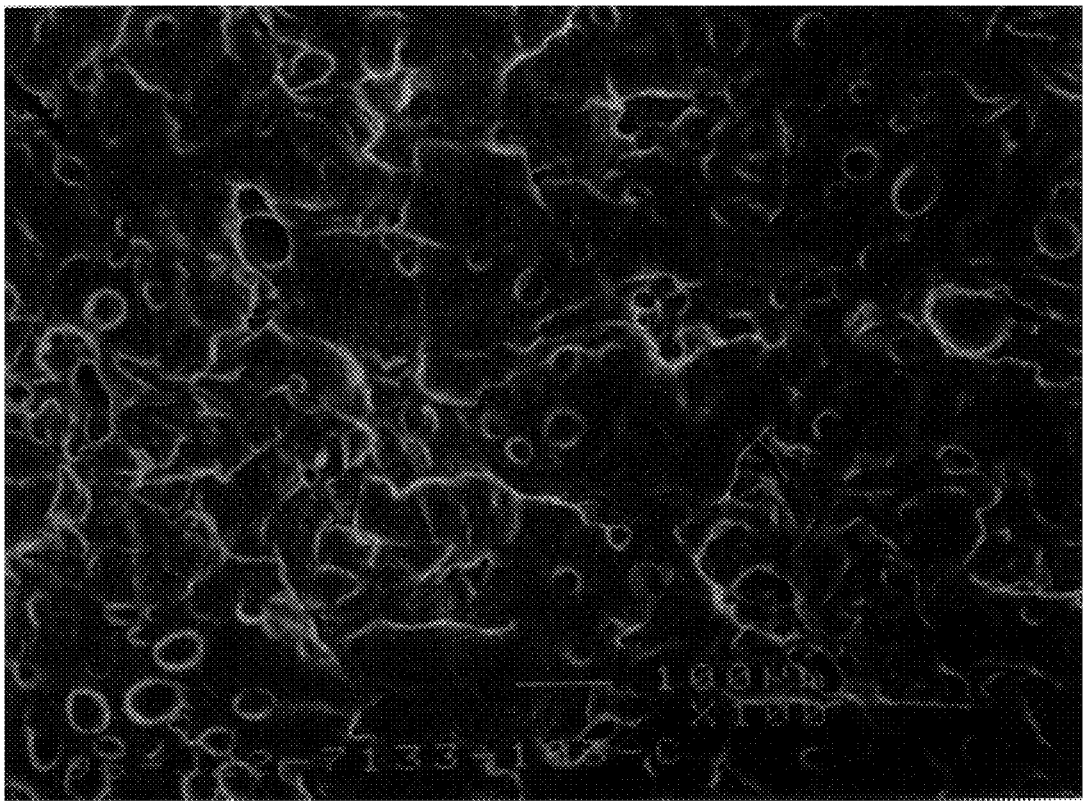
FIG. 11 is an SEM photograph at ×100 magnification of the inner surface of prosthesis sample 103-C of Example 2 that was formed by electrostatically co-spraying silicone fibers and fibers comprising solid PEG having a molecular weight of 8000 onto a rotating mandrel.
Figure 12:
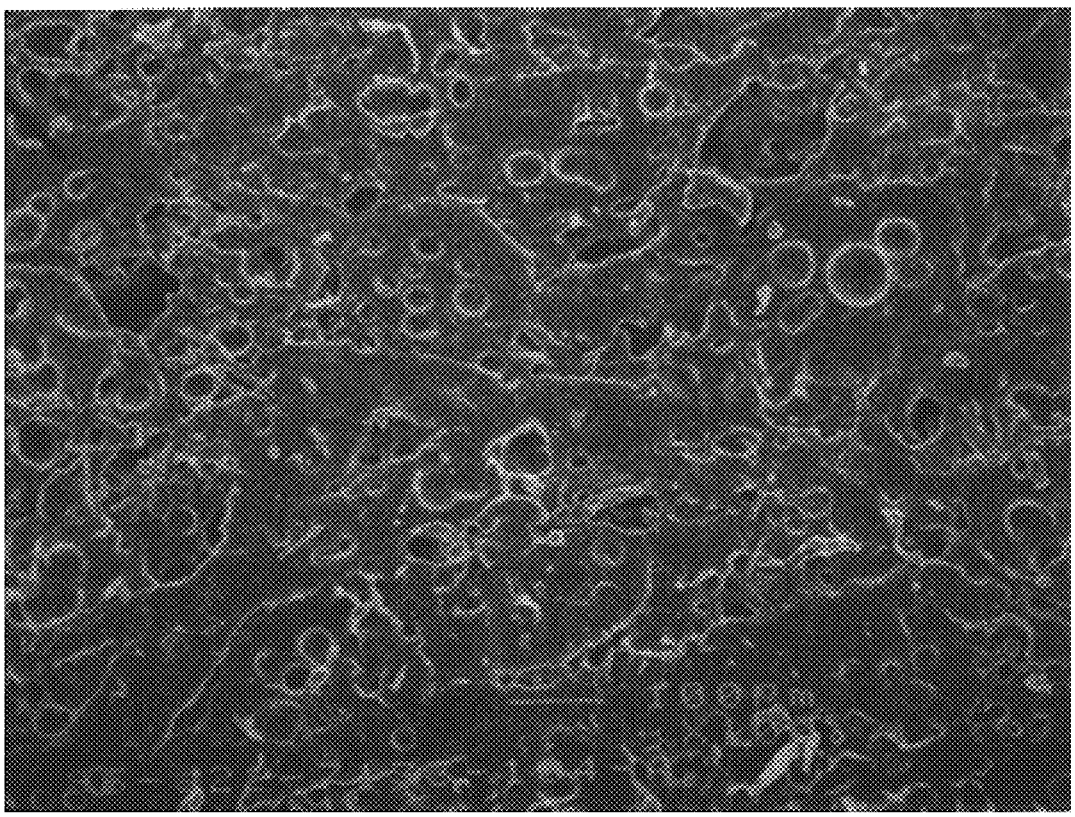
FIG. 12 is an SEM photograph at ×100 magnification of the inner surface of prosthesis sample 104-A of Example 2 that was formed by electrostatically co-spraying silicone fibers and fibers comprising solid PEG having a molecular weight of 8000 onto a rotating mandrel.
Figure 13:
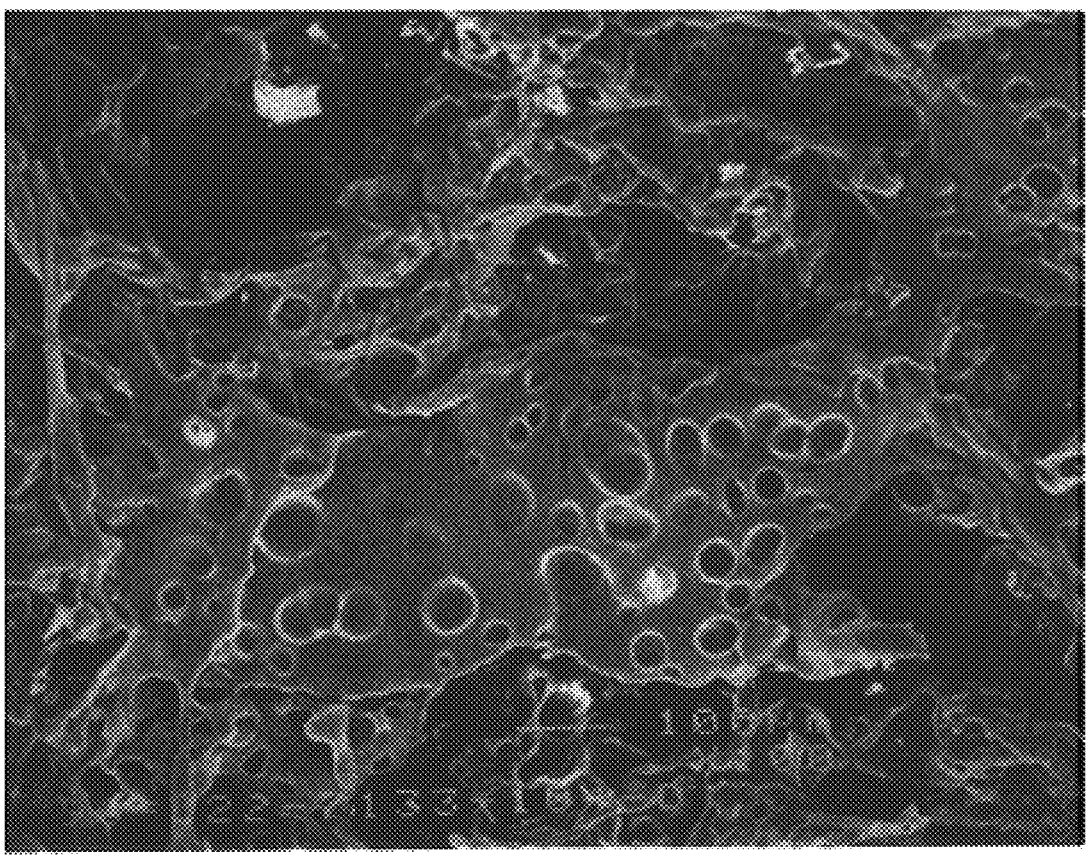
FIG. 13 is an SEM photograph at ×100 magnification of the inner surface of prosthesis sample 104-D of Example 2 that was formed by electrostatically co-spraying silicone fibers and fibers comprising solid PEG having a molecular weight of 8000 onto a rotating mandrel.
Figure 14:
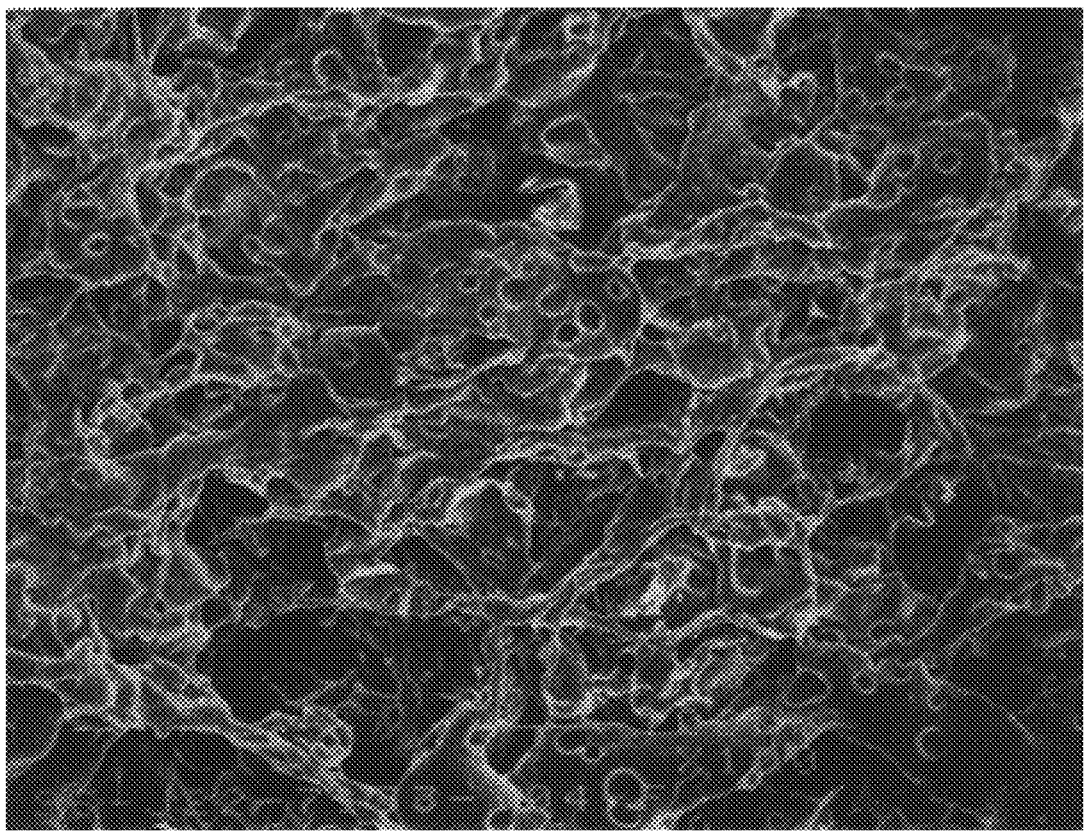
FIG. 14 is an SEM photograph at ×100 magnification of the inner surface of prosthesis sample 104-F of Example 2 that was formed by electrostatically co-spraying silicone fibers and fibers comprising solid PEG having a molecular weight of 8000 onto a rotating mandrel.

FIG. 6 shows another approach in which the principles of the present invention may be practiced to form prosthesis 9 having a desired level of inner porosity. As an overview, this approach is similar to that of FIGS. 1–4, except that fibrous components 34 and 35 are co-sprayed around mandrel 12 bearing water soluble coating 36. The presence of this coating makes it significantly easier to remove prosthesis 9 from mandrel 12. Coating 36 also may further help to prevent water insoluble fibrous component 34 from coalescing on mandrel 12 after spraying to some degree.

In preferred embodiments, the water soluble material incorporated into coating 36 may be any water soluble, organic, solid or semisolid material under the conditions at which electrostatic spraying is carried out. Preferably, such water soluble material may further comprise properties effective to help reduce the tendency of portions of fiber component 34 to coalesce around mandrel 12. Representative examples of such materials include one or more oligomeric or polymeric materials selected from polyethylene glycols (PEG) preferably having a weight average molecular weight in the range from 1000 to about 10,000; polyvinyl alcohol; polyacrylamide; poly(methylvinyl ether); polyacrylic acid; poly(vinylpyridine); esters of poly(meth) acrylic acid wherein the ester group may be represented by the formula —OR in which the R moiety is sufficiently small (e.g., methyl or ethyl or other $C_1$ or $C_2$ type of moiety) so that the polymer is water soluble; similar esters of polyvinyl alcohol; combinations of these, and the like. Most preferably, the water soluble material is PEG, more preferably PEG having a weight average molecular weight of about 8000.

To help make coating 36 more uniform and smooth, coating 36 may be heated prior to electrostatic spraying operations. Preferably, coating 36 may be heated to a temperature close to, more preferably slightly above, the glass transition temperature of the material(s) constituting coating 36 so that the material of coating 36 at least partially melts to provide a smooth, even, uniform coatable surface upon which to form prosthesis 9. When coating 36 comprises PEG having a weight average molecular weight of about 8000 (PEG 8000), a 250 Watt IR lamp can be placed about 190 mm away from mandrel 12 to accomplish heating.

Coating 36 may be applied onto mandrel 12 in any convenient form such as a melt, a solution, or a dispersion, as desired. The particular technique used to apply coating 36 is not critical and any suitable coating technique may be used, including brushing, dip coating, spraying, and the like. If coating 36 is applied as a solution or dispersion, the solution or dispersion preferably contains a sufficient amount of solvent so that the solution or dispersion has a viscosity suitable for the application technique being used. Most typically, such a solution or dispersion may comprise 20 to 150 parts by weight of elutable material per about 80 parts by weight of solvent. For example, one preferred solution for forming coating 36 may comprise about 120 parts by weight of PEG 8000 and about 80 parts by weight of solvent.

A wide range of solvents may beneficially be incorporated into the solution or dispersion that is used to form coating 36. These include, for example, dichloromethane, water, alcohols, combinations of these, and the like, of which water, alcohols or combination of these are preferred. After the solution or dispersion is applied to mandrel 12, coating 36 may be dried before carrying out electrostatic spraying operations. Once coating 36 is formed on mandrel 12, electrostatic spraying operations may be carried out as described above with respect to FIG. 1.

The present invention will now be described with respect to the following illustrative examples. In the examples and throughout this specification, the following test methods and calculations were used unless otherwise noted:

Test Procedure 1. Inside Diameter

The inside diameter of a prosthesis was estimated from measurements of the outside diameter of the mandrel that were made using a calibrated digital caliper.

Test Procedure 2. Wall Thickness

The wall thickness of a prosthesis was determined using an OPTIMUS Optical Image Analyzer with a NIKON MIIA 11122 Microphot F/X magnification of X150 and a calibrated graticule. A cross-section of a prosthesis was placed on a microscope slide using reflected light. The top surface of the prosthesis cross-section was brought into focus. Six wall thickness measurements in micrometers were taken at approximately equal distances around the circumference of the prosthesis. An average and a standard deviation were recorded for each prosthesis tested.

Test Procedure 3. Porosity

The porosity of a prosthesis was determined as follows. First, the length of the prosthesis was measured using a ruler. A sample portion of the prosthesis was then weighed using a Mettler digital balance (MII#A08928). The weight was recorded in grams. The inside diameter and wall thickness measurements obtained previously were converted to centimeters. A total volume in cubic centimeters for the portion of the prosthesis chosen for porosity testing was calculated using the following formula for a tube where h is the length:

$$V = \pi \times h \times (r_2^2 - r_1^2)$$

The porosity of the prosthesis was then determined by the following calculation:

$$\text{Porosity} = \{1 - [\text{weight}/(\text{density of polymeric resin component})]/\text{volume}\} \times 100\%$$

Preferably, a prosthesis of the present invention exhibits porosity on at least the inner wall surface of the prosthesis, more preferably on both the inner and outer wall surfaces of the prosthesis. More preferably, the prosthesis further exhibits a sufficient level of porosity on at least the inner wall surface to benefit from cellular ingrowth and fixation of the prosthesis upon implantation. The level of porosity will depend upon the particular application in which prosthesis 9 will be used. Generally, a beneficial amount of porosity may be in the range from 5% to 95%. As one specific example, and in accordance with current clinical practice, a vascular prosthesis preferably has a porosity of 60% to 85%, more preferably 70% to 80%. In contrast, a prosthesis to be used for drug delivery applications may have higher porosity levels, e.g., 80% to 95%.

Test Procedure 4. Elongation Versus Outer Diameter

The outside diameter of a prosthesis was determined at several elongations. Two dots, two centimeters apart, were marked in the middle of a prosthesis. The outside diameter between the two dots was measured with a meterstick placed perpendicular to the prosthesis and was recorded as the outside diameter at 0% elongation.

The prosthesis was then stretched to a pre-determined elongation, and an outside diameter between the two dots was again recorded. The pre-determined elongation was obtained by placing two dots on a piece of paper for the two dots on the prosthesis to be matched against. For example, for 100% elongation, the two dots on the prosthesis originally 2 cm apart would be stretched to match two dots on the paper that were 4 cm apart. Outside diameters were obtained at elongations of 0, 10, 25, 50, 100 and 150%.

Test Procedure 5. Longitudinal Tensile Strength

The longitudinal force to break and percent strain at break were determined for a prosthesis using an Instron tester with a 50 lb. (22.65 kg) tensile load cell. Pneumatic-operated grips with rubber facings were used to hold the sample (10±0.1 cm long), with a grip separation 50±1 mm. A crosshead speed of 100±1 mm/minute was used to raise the upper jaw until the prosthesis specimen failed. The maximum force in kilograms and the force in kilograms per thickness to break the prosthesis were recorded, along with % strain at break.

Test Procedure 6. Radial Tensile Strength

The radial force at break and the deflection at break were determined for a prosthesis using an Instron tester with a 50 lb. (22.65 kg) tensile load cell. Split bar jaws were used to hold a prosthesis sample (1.27 cm long). A crosshead speed of 50±1 mm/minute was used until the prosthesis specimen failed. The maximum force in kilograms/cm$^2$ to break the prosthesis was recorded, along with the deflection at break.

Test Procedure 7. Scanning Electron Microscopy (SEM)

The inner and outer surfaces of a prosthesis were analyzed using scanning electron microscopy (SEM) using a JEOL JSM 6400 scanning electron microscope. Specifically, a small piece of prosthesis (approximately 1 cm) was cut open. A small portion of this section of prosthesis was then affixed to an SEM mount using two sided tape. The sample was then gold-coated prior to analysis. SEM photomicrographs were obtained of the surfaces at two magnifications, 30 and 100×.

EXAMPLE 1

Production of Silicone Prostheses

Three prostheses samples of the present invention were made using the co-spraying process described above with respect to FIGS. 1 and 2. Fiber forming composition 32 comprised the 40016 grade silicone manufactured by Applied Silicone Technology. The silicone was received as a 29% solids solution in trichloroethane. To provide fiber forming composition 32, this silicone solution was dried to 80% solids to remove most of the trichloroethane (TCE) and then diluted with dichloromethane (DCM) to obtain a 20% solids solution. Fiber forming composition 33 comprised a 60% solids PEG 8000 (i.e., a PEG with a weight average molecular weight of 8000, which is a solid under the processing conditions when neat) solution in DCM. For comparison purposes, a comparative prostheses was pre pared in which a PEG (PEG 600) having a molecular weight of 600 (a liquid under the processing conditions) was substituted for the PEG 8000. Each of cylinders 42 and 43 used in this example and all the other examples was in the form of a 10 cc syringe equipped with a 25 gauge shortened needle. The syringes were centrifuged prior to forming the prostheses to remove air bubbles which might have developed when the syringes were filled. The solutions were pumped out of the syringes at differing flow rates as shown in Table I. The process conditions at which the prostheses were produced are summarized in Table II. All four samples were dried at room temperature for two hours to remove residual solvent, cured in an oven at 150° C. for 30 minutes, and immersed in boiling water to wash out any residual PEG.

thesis sample #99-A even had fibers extending out from the surface. These exterior fibers were gently pressed in by rolling the prosthesis on a clean, flat surface.

EXAMPLE 2

Production of Silicone Prostheses by Electrostatic Co-Spraying in the presence of PEG The procedure of Example 1 was repeated except that the processing conditions of Table III and IV were used. A total of four prosthesis samples of the present invention were made. The prosthesis samples produced were tested for dimensions, porosity, mechanical properties, and examined under SEM.

TABLE I

Prosthesis Sample Identification as per Silicone/PEG Ratio

| Prosthesis Sample Identification | PEG Type | PEG Solids Content | PEG Flow Rate (cc/min) | Silicone Flow Rate (cc/min) | PEG/ Silicone Ratio | Spinning Time (Min) | |
|---|---|---|---|---|---|---|---|
| | | | | | | PEG | Silicone |
| 99-A | 600 | 100% | 0.2 | 0.3 | 3:1 | 55 | 60 |
| 99-B | 8000 | 60% | 0.1 | 0.3 | 1:1 | 65 | 60 |
| 100-A | 8000 | 60% | 0.2 | 0.2 | 3:1 | 55 | 90 |
| 100-B | 8000 | 60% | 0.1 | 0.2 | 1.5:1 | 65 | 90 |

TABLE II

Process Conditions for Prosthesis Production

| | |
|---|---|
| Silicone Solids Content (%): | 20 |
| Spinneret-Mandrel Distance (mm): | 150 |
| Electrostatic Voltage (KV): | 45.5 |
| Mandrel Rotational Speed (rpm): | 1500 |
| Mandrel Transverse Speed (cm/min): | 401 |
| Needle Size (gauge): | 25 |
| Needle Length (mm): | 3.0 |

TABLE III

Prosthesis Sample Identification

| Prosthesis Sample Identification | PEG Flow Rate (cc/min) | Silicone Flow Rate (cc/min) | PEG/Silicone Ratio | Spinning Time (Min) |
|---|---|---|---|---|
| 103-C | 0.05 | 0.5 | 0.2:1 | 35 |
| 104-A | 0.1 | 0.4 | 0.5:1 | 45 |
| 104-D | 0.15 | 0.3 | 1:1 | 65 |
| 104-F | 0.2 | 0.2 | 2:1 | 95 |

SEM photos were taken (magnification ×100) on the inner surfaces of samples 99-A, 99-B, 100-A, and 100-B (FIGS. 7–10, respectively). FIGS. 7–10 show that co-spraying with PEG helped impart porosity at the inner surface of prostheses, and thus contributed to the overall porosity of the prosthesis. Sample 100-A had the highest porosity. The PEG/Silicone weight ratio of this sample was 3:1.

In contrast, comparative sample 99A was unsatisfactory. Droplets of this liquid PEG were attracted to the mandrel by electrostatic action, but these were then ejected from the rotating mandrel by centrifugal forces. Comparative pros-

TABLE IV

Process Conditions for Prosthesis Production

| | |
|---|---|
| PEG Solids Content (%): | 40 |
| Silicone Solids Content (%): | 20 |
| Spinneret-Mandrel Distance (mm): | 150 |

TABLE IV-continued

Process Conditions for Prosthesis Production

| | |
|---|---|
| Electrostatic Voltage (KV): | 45.5 |
| Mandrel Rotational Speed (rpm): | 1500 |
| Mandrel Transverse Speed (cm/min): | 401 |
| Needle Size (gauge): | 25 |
| Needle Length (mm): | 3.0 |

SEM photos were taken (magnification ×100) on the inner surfaces of samples 103-C, 104-A, 104-D and 104-F (FIGS. 11–14, respectively). Again, the photos show that the method of the present invention provided prostheses with porous inner surfaces. The photos also show that the porosity of the inner surface of the prostheses increased as the PEG/silicone weight ratio increased.

The results for porosity and mechanical properties evaluations are reported in Tables V and VI:

TABLE V

Porosity of PEG/Silicone Prostheses

| Sample Prosthesis Identification | PEG/Silicone Ratio | Wall Thickness (mm) | Porosity (%) |
|---|---|---|---|
| 103-C | 0.2:1 | 0.3904 | 22.6 |
| 104-A | 0.5:1 | 0.4890 | 40.4 |
| 104-D | 1:1 | 0.7031 | 66.6 |
| 104-F | 2:1 | 0.4340 | 53.2 |

As is shown by the data in Table V, the porosity of the PEG/silicone prostheses increased as the weight ratio of PEG/silicone increased.

TABLE VI

Mechanical Properties

| Sample Prosthesis Identification | Radial Tensile Properties | | Longitudinal Tensile Properties | | PEG/Silicone Ratio |
|---|---|---|---|---|---|
| | Norm. Load at Break (kg/cm²) | Deflection at Break (mm) | Norm. Max. Load (kg/cm) | % Strain at Break (%) | |
| 103-C | 18.35 | 71.7 | 16.09 | 560 | 0.2:1 |
| 104-A | 4.77 | 49.3 | 6.38 | 390 | 0.5:1 |
| 104-D | 1.00 | 35.8 | 1.41 | 320 | 1:1 |
| 104-F | 1.10 | 47.1 | 1.71 | 270 | 2:1 |

As shown in Table VI, the prosthesis obtained using the lowest PEG/silicone weight ratio (i.e., 0.2:1) exhibited the highest load at break and deflection at break.

The percent decrease in the outside diameter of the prostheses was recorded at different elongations. See Tables VII and VIII, below. This data shows that, at any specific elongation, smaller outside diameters were obtained as the PEG/Silicone weight ratio was increased.

TABLE VII

Outside Diameter (cm) vs. % Elongation

| Sample Prosthesis Identification | OUTSIDE DIAMETER (cm) % Elongation | | | | | |
|---|---|---|---|---|---|---|
| | 0 | 10 | 25 | 50 | 100 | 150 |
| 103-C | 0.75 | 0.70 | 0.70 | 0.65 | 0.55 | 0.50 |
| 104-A | 0.75 | 0.75 | 0.75 | 0.70 | 0.65 | 0.60 |
| 104-D | 0.85 | 0.85 | 0.80 | 0.75 | 0.70 | 0.65 |
| 104-F | 0.85 | 0.85 | 0.85 | 0.85 | 0.80 | 0.75 |

The data of Table VII was normalized and converted to percentages, with the initial diameter being the reference. The normalized data is shown in Table VIII, below.

TABLE VIII

Outside Diameter (cm) vs. % Elongation

| Sample Prosthesis Identification | OUTSIDE DIAMETER (cm) % Elongation | | | | | |
|---|---|---|---|---|---|---|
| | 0 | 10 | 25 | 50 | 100 | 150 |
| 103-C | 100 | 93.3 | 93.3 | 86.7 | 73.3 | 66.7 |
| 104-A | 100 | 100 | 100 | 93.3 | 86.7 | 80.0 |
| 104-D | 100 | 100 | 94.1 | 88.2 | 82.4 | 76.5 |
| 104-F | 100 | 100 | 100 | 100 | 94.1 | 88.2 |

The above experiments show that the electrostatic co-spraying process of the present invention is an effective way of producing porous silicone prostheses.

Comparative Example A

Production of a Silicone Prosthesis without Co-Spraying

This experiment was conducted to evaluate the impact of different operating parameters on the porosity of the prosthesis produced by electrostatic spraying, using only a silicone fiber instead of both silicone and PEG fibers. Two comparative prostheses samples were prepared following the procedure of Example 1, except that the silicone fiber was wound around the mandrel by itself, and the processing conditions of Tables IX and X were used (In Table IX, RT means room temperature). For one of the samples, the mandrel was preheated prior to winding by holding a heat gun at a distance of 10 cm from the mandrel.

TABLE IX

Prosthesis Sample Identification as per Preheating, Drying and Curing Conditions

| Prosthesis Sample Identification | Mandrel Preheating | Drying Conditions | Curing Conditions |
|---|---|---|---|
| 93-A | No | RT for 2 days | 50° C. for 3 hrs + 150° C. for 30 min. |
| 93-B | Yes | RT for 2 hours | 150° C. for 30 min. |

TABLE X

Process Conditions for Prosthesis Production

| | |
|---|---|
| Spinneret-Mandrel Distance (mm): | 150 |
| Electrostatic Voltage (KV): | 43 (A) and 46.5 (B) |
| Flow Rate (cc/min): | 0.3 |
| Mandrel Rotational Speed (rpm): | 1500 |
| Mandrel Transverse Speed (cm/min): | 401 |
| Needle Size (gauge): | 25 |
| Needle Length (mm): | 3.0 |
| Spinning Time (hr): | 1.0 |

Figure 15:
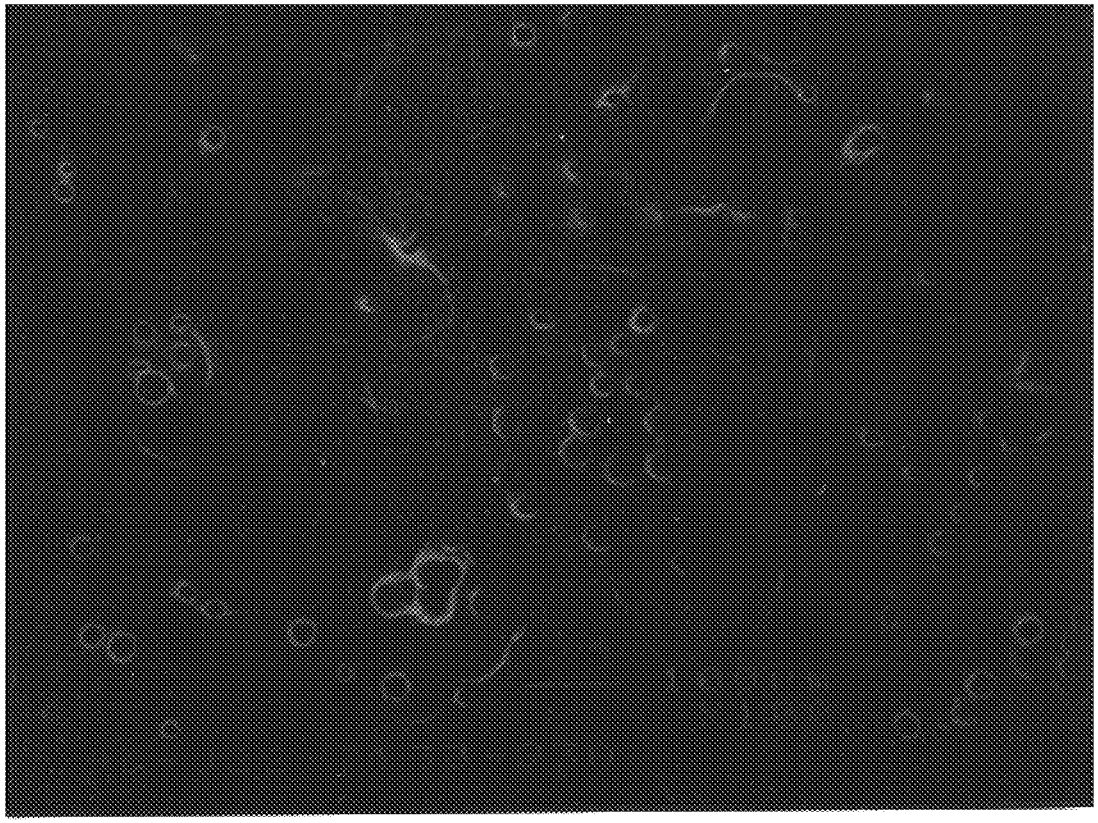
FIG. 15 is an SEM photograph at ×100 magnification of the inner surface of prosthesis sample 93-A of Comparative Example A formed by electrostatically spraying silicone fibers around a rotating mandrel.
Figure 16:
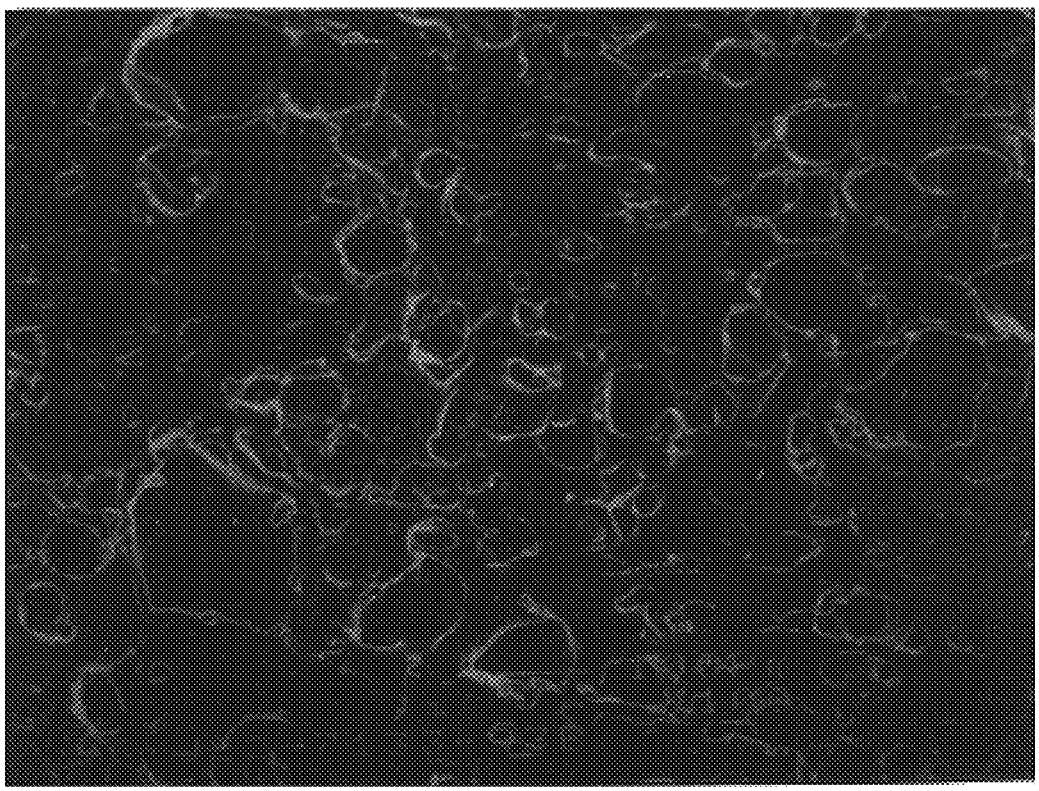
FIG. 16 is an SEM photograph at ×100 magnification of the inner surface of prosthesis sample 93-B of Comparative Example A formed by electrostatically spraying a silicone fiber around a pre-heated, rotating mandrel.

SEM photos were taken (magnification ×100) on the inner surfaces of samples 93-A and 93-B (FIGS. 15–16, respectively). The inner surface of sample #93-A exhibited a more or less uniform solid film pattern (FIG. 15). Preheating the mandrel prior to spinning resulted in a slightly porous prosthesis (sample #93-B, FIG. 16), although the level of porosity was still inadequate. As is shown by these results, a sufficiently porous prosthesis was not obtained by electrostatic spraying of silicone alone, even when the mandrel was preheated Comparative Example B Production of a Silicone Prosthesis without Co-Spraying Using a Higher Viscosity Silicone Rubber For the following experiment, a silicone elastomer (MED-4070 grade for restricted applications) from Nusil Silicone Technology was selected for its combination of high hardness/durometer value (70 shore A) and high viscosity.

This two-part system silicone (100% solids content) was not very soluble in DMC. Therefore, pentane was used as a solvent to prepare a 20% solids solution. The solution was spun on rotating mandrel and a solid, nonporous film was obtained. To see if a more dilute solution might work better, a 30% solids solution of the same rubber in pentane was prepared and spun onto a rotating mandrel. Again, a nonporous prosthesis was obtained. Thus, it was concluded that the use of a higher viscosity silicone elastomer does not result in a porous prosthesis.

Other embodiments of this invention will be apparent to those skilled in the art upon consideration of this specification or from practice of the invention disclosed herein. Various omissions, modifications, and changes to the principles and embodiments described herein may be made by one skilled in the art without departing from the true scope and spirit of the invention which is indicated by the following claims.

What is claimed is:

1. A method of making a porous, tubular, synthetic prosthesis, comprising the steps of:

(a) electrostatically co-spraying ingredients comprising a water soluble fibrous component and a water insoluble fibrous component onto a mold to form a prosthesis precursor, wherein the water soluble fibrous component functions as a spacer to inhibit coalescence of the water insoluble fibrous component on the mold; and (b) removing at least a portion of the water soluble fibrous component from the precursor to form the prosthesis, said prosthesis comprising fibrous-shaped voids.

2. A method of making a tubular prosthesis precursor, comprising the step of co-spraying a water insoluble, fibrous component and a water soluble fibrous component onto a mold to form the tubular prosthesis precursor comprising a water soluble fibrous component and a water insoluble fibrous component.

3. The method of claim 1, wherein the mold is a rotating mandrel.

4. The method of claim 1, wherein step (b) comprises eluting the water soluble fibrous component by washing the tubular prosthesis precursor with an eluent.

5. The method of claim 4, wherein the eluent is water.

6. The method of claim 1, wherein the prosthesis precursor is tubular and wherein step (b) comprises removing a sufficient amount of the water soluble, fibrous component from the precursor such that the prosthesis has an inner wall surface with a sufficient amount of porosity to promote the ingrowth of tissue when the prosthesis is therapeutically implanted in a host.

7. The method of claim 1, wherein the prosthesis has a porosity in the range from about 5% to about 95%.

8. The method of claim 7, wherein the prosthesis has a porosity of from about 60% to about 95%.

9. The method of claim 8, wherein the prosthesis has a porosity of from about 70% to about 80%.

10. The method of claim 1, wherein the prosthesis mold is a rotating mandrel, and said co-spraying step comprises electrostatically co-spraying the water insoluble and water soluble fibrous components onto the rotating mandrel from first and second orifices, respectively, and wherein the first and second orifices are caused to translate axially back and forth relative to the mandrel such that the fibrous components coat the mandrel to form said precursor.

11. The method of claim 10, wherein the co-spraying step comprises the steps of:

(i) extruding a first composition comprising a water insoluble silicone resin through the first orifice to form the water insoluble fibrous component; and (ii) extruding a second composition comprising a water soluble polyethylene glycol through the second orifice to form the water soluble fiber component.

12. The method of claim 11, wherein the polyethylene glycol has a weight average molecular weight of at least 1000.

13. The method of claim 12, wherein the polyethylene glycol has a weight average molecular weight in the range from about 1000 to about 15,000.

14. The method of claim 11, wherein the first composition further comprises a solvent in which the silicone resin is substantially completely soluble, said solvent comprising first and second solvent components, wherein the first solvent component has a boiling point at least 10° C. greater than that of the second solvent component.

15. The method of claim 14, wherein the first solvent component has a boiling point at least 25° C. greater than that of the second solvent component.

16. The method of claim 14, wherein the weight ratio of the second solvent component to the first solvent component is in the range of from about 2:1 to about 10:1.

17. The method of claim 14, wherein the solvent comprises a halogenated alkane solvent selected from a trihaloethane, a dihaloethane, a trihalomethane, a dihalomethane, or combinations of these.

18. The method of claim 17, wherein the solvent comprises 1 to 20 parts by weight dichloromethane and 1 to 20 parts by weight of trichloroethane.

19. The method of claim 1, wherein the weight ratio of the water insoluble fibrous component to the water soluble fibrous component is in the range of from about 1:10 to about 5:1.

20. The method of claim 19, wherein the weight ratio of the water insoluble fibrous component to the water soluble fibrous component is in the range of from about 1:3 to about 1:2.

21. The method of claim 1, wherein the co-spraying step comprises co-spraying both the water insoluble and water soluble fibrous components onto the mold to build up an inner portion of the tubular prosthesis precursor, and wherein the method further comprises the steps of:
(i) ceasing to spray the water soluble fibrous component onto the mold when said inner portion is formed, and
(ii) after ceasing to spray the water soluble fibrous component onto the mold, continuing to spray the water insoluble fibrous component onto the mold until said tubular prosthesis precursor body is formed.

22. The method of claim 1, further comprising the step of, prior to co-spraying said fibrous components onto the mold, coating the mold with a coating comprising polyethylene glycol.

* * * * *